US 6,750,247 B2

(12) United States Patent
Crews et al.

(10) Patent No.: US 6,750,247 B2
(45) Date of Patent: Jun. 15, 2004

(54) SPONGE-DERIVED TERPENOIDS AND METHODS OF USE

(75) Inventors: Phillip Crews, Santa Cruz, CA (US); Jennifer Carroll, Santa Cruz, CA (US); Theodore Holman, Santa Cruz, CA (US); Guy Miller, Santa Clara, CA (US); Steve Bobzin, Santa Clara, CA (US); Lesley Brown, Santa Clara, CA (US)

(73) Assignee: Galileo Laboratories, Inc., Santa Clara, CA (US)

( * ) Notice: Subject to any disclaimer, the term of this patent is extended or adjusted under 35 U.S.C. 154(b) by 0 days.

(21) Appl. No.: 10/159,772

(22) Filed: May 31, 2002

(65) Prior Publication Data

US 2003/0065025 A1 Apr. 3, 2003

Related U.S. Application Data

(60) Provisional application No. 60/295,258, filed on May 31, 2001.

(51) Int. Cl.[7] .................. A61K 31/19; A61K 31/34; A61K 31/35; C07C 63/66; C07D 307/42; C07D 311/70

(52) U.S. Cl. .................. 514/456; 514/461; 514/569; 549/407; 549/502

(58) Field of Search .................. 549/407, 502, 549/506, 408; 562/466; 514/456, 461, 569

(56) References Cited

U.S. PATENT DOCUMENTS

| 4,447,445 | A | 5/1984 | Jacobs et al. |
|---|---|---|---|
| 4,943,589 | A | 7/1990 | Crews et al. |
| 5,162,365 | A | 11/1992 | Chinn et al. |
| 5,208,364 | A | 5/1993 | Ohkuma et al. |
| 5,563,292 | A | 10/1996 | Shih et al. |
| 5,648,376 | A | 7/1997 | Strobel et al. |
| 6,069,146 | A | 5/2000 | Fenical et al. |

FOREIGN PATENT DOCUMENTS

| WO | WO 98/00168 | 1/1998 |
|---|---|---|
| WO | WO 98/01134 | 1/1998 |

OTHER PUBLICATIONS

Jaspara, et al, "The Cyclorenierins, Sesquiterpenoid Quinols from the Sponge Haliclona SP. Collected in Vanuatu"; Journal of Natural Products, vol. 58, No. 4, pp. 609–612; Apr. 1995.

DE Vries, et al, "Preferenctal Inhibition of 5–Lipoxygenase Activity by Manoalide"; Biochemical Pharmacology, vol. 37, No. 15, pp. 2899–2905, 1988.

CABRE' et al, "Effect of Manolalide on Human 5–lipoxygenase Activity", Inflamm Re. 45: 218–223(1996); Original Research Paper.

Look, et al, The Pseudopterosins: A New Class of Antiinflammatory and Analgesic Diterpene Pentosides from the Marine Sea Wip Pseudopterogorgia elisabethae (Octocorallia); J. Org. Chem. 1986, 51, pp. 5140–5145.

Muyer, et al, Pharmacological Characterization of the Pseudopterosins: Novel Anti–Inflammatory Natural Products Isolated from the Caribbean Soft Coral, Pseudopterogorgia elisabethae; Life Sciences, vol. 62. No. 26, pp. Pl. 401–407, 1998.

Jacobson, et al., "Fuscoside: An Anti–Inflammatory Marine Natural Product which Selectively Inhibits 5–Lipoxygenase. Part I: Physiological and Biochemical Studies in Murine Inflammatory Models", The Journal of Pharmacology and Experimental Therapeutics, vol. 262, No. 2 pp. 866–873.

Kazlauskas, et al., "Heteronemin, A New Scalarin Type Sesterterpene for the Sponge Heteronema Erecta", Tetrahedron Letters, No. 30, pp. 2631–2634, 1976.

Hoang Tran, et al., New Oxygenated Sesquiterpenes from a Southern Australian Marine Sponge, Dictyodendrilla sp. Aust. J. Chem, 1995, 48, pp. 1757–1760.

Fu, et al., Halisulfate 7, a New Sesterterpene Sulfate from a Sponge, Coscinoderma sp. J. Nat. Prod. 1999, 62, pp. 1190–1191.

Murray, et al. "Geographic Variation in the Tropical Marine Sponge Jaspis cf. johnstoni: An Unexpected Source of New Terpene–Benzenoids" J. Org. Chem 1997, 62, pp. 5638–5641.

Tasdemir, et al., entitled *"New Terpenoids from a Cacospongia sp. From the Philippines,"* Tetrahedron 56 (2000) 9025–9030.

Tasdemir, et al., entitled *"Corrigendum to "New Terpenoids from a Cacospongia sp. From the Philippines" Tetrahedron 56 (2000) 9025–9030,"* Tetrahedron 56 (2001) 5681.

Primary Examiner—Bernard Dentz
(74) Attorney, Agent, or Firm—Carol L. Francis; Bozicevic, Field & Francis LLP

(57) ABSTRACT

Compounds that are effective lipoxygenase inhibitors, and methods and pharmaceutical compositions for inhibiting lipoxygenases and for treatment of lipoxygenase-mediated conditions in humans and other subjects. The compounds, methods and pharmaceutical compositions utilize subersic terpenoids, jaspic terpenoids, igernellic terpenoids, hippospongic terpenoids, halicondric terpenoids, dictyodendric terpenoids, and/or heteronemic terpenoids, and synthetic derivatives or analogs thereof. Exemplary compounds include (−)-subersic acid, (+)-subersin, jaspaquinol, (−)-jaspic acid, igernellin, halisufate 7, and hipposulfate C and D, and derivatives thereof.

9 Claims, No Drawings

SPONGE-DERIVED TERPENOIDS AND METHODS OF USE

CROSS REFERENCE TO RELATED APPLICATIONS

This application is entitled to the benefit of U.S. Provisional Application Ser. No. 60/295,258 filed on May 31, 2001, the disclosure of which is incorporated herein by reference.

STATEMENT REGARDING FEDERALLY SPONSORED RESEARCH

This invention was made with Government support under Grant No. NA66RG0477, awarded by the National Oceanic & Atmospheric Admin. The Government may have certain rights in this invention.

BACKGROUND OF THE INVENTION

Lipoxygenases are non-heme iron dioxygenase enzymes, which catalyze the hydroperoxidation of dieneoic and polyenoic fatty acids. Lipoxygenases are ubiquitous in mammals and include the 5-, 12-, and 15-lipoxygenases which respectively catalyze the insertion of oxygen at the C-5, C-12 and C-15 positions of arachidonic acid. The resulting leukotrienes and lipoxins provide signaling molecules associated with a variety of human diseases such as asthma, atherosclerosis, psoriasis and inflammatory bowel disease. Selective inhibitors for the human lipoxygenases thus are potentially useful as pharmacological agents, neutraceuticals and/or molecular tools.

Marine natural products have provided a variety of bioactive compounds, but relatively few marine natural products have been noted as being lipoxygenase inhibitors. The pseudopterosins are diterpene glycosides found in the Caribbean sea whip *Pseudopterogorgia elisabethae*, believed to have anti-inflammatory properties related to inhibition of cycloxygenase and lipoxygenase biosynthetic pathways (Look et al., *J. Org. Chem.* 1986, 51, 5140; Jacobs et al., *Pharm. Lett.* 1998, 62, 401). Fuscosides, which are diterpenoid glycosides from marine gorgonia, also have anti-inflammatory properties believed to be associated with lipoxygenase inhibition (Jacobsen et al., *J. Pharmacol. Exp. Ther.* 1992, 262, 866).

The only sponge-derived lipoxygenase inhibitors to date are pentabromo biphenyl ethers (Fu et al., *J. Nat. Prod.* 1995, 58, 609) isolated from cyanobacterial-containing sponges. The anti-inflammatory compound manoalide from *Luffariella variabilis* was initially identified as an inhibitor of 5-lipoxygenase (Devries et al., *Biochem. Pharmacol.* 1988, 37, 2899), but the available 5-lipoxygenase assay used has been problematic, and subsequent studies (Cabre et al., *Inflamm. Res.* 1996, 45, 218) show that manoalide has no lipoxygenase inhibitory properties.

There is a need for new selective inhibitors of human lipoxygenases, as well as other anti-inflammatory bioactive compounds usable for treatment of conditions associated with lipoxygenase and other conditions and diseases. The present invention satisfies these needs, as well as others, and overcomes deficiencies found in the background art.

SUMMARY OF THE INVENTION

The invention provides new compounds that are effective lipoxygenase inhibitors and effective therapeutic agents for methods and treatments for lipoxygenase mediated conditions and other diseases, disorders and conditions. The invention also provides pharmaceutical compositions and methods for inhibiting human lipoxygenases, treatments for lipoxygenase mediated conditions, and treatments for other diseases, disorders and conditions. The invention further provides pharmaceutical compositions and methods for increasing cell viability and prevention of cell damage associated with ischemia or hypoxic or anoxic events, and for treatment of ischemia, stroke, and inflammatory conditions generally.

The subject compounds, pharmaceutical compositions and methods comprise, or comprise the use of, subersic terpenoids, jaspic terpenoids, igemellic terpenoids, hippospongic terpenoids, halicondric terpenoids, dictyodendric terpenoids, and/or heteronemic terpenoids.

In some embodiments of the invention, the subject compounds, pharmaceutical compositions and methods may comprise or utilize compounds having the structure:

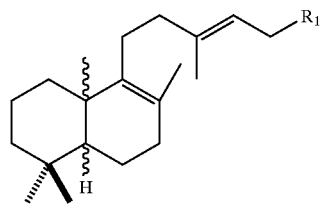

wherein $R_1$ comprises

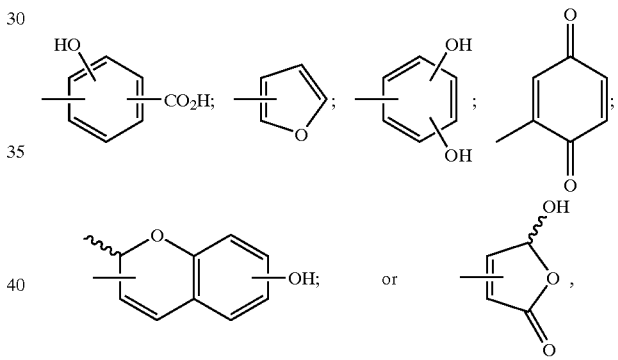

and individual isomers, racemic or non-racemic mixtures of isomers, and pharmaceutically acceptable salts thereof. In specific embodiments, the compounds, pharmaceutical compositions and methods may comprise or utilize (−)-(5R, 10R)-subersic acid, also named 4-hydroxy-3-[3-methyl-5-(2,5,5,8a-tetramethyl-3,4,4a,5,6,7,8,8a-octahydro-naphthalen-1-yl)-pent-2-enyl]-benzoic acid (1):

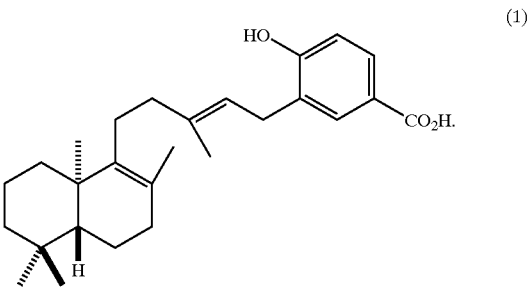

Substantially purified or isolated subersic terpenoid compounds isolated from Suberea sp. (Order: Verongida, Family: Aplysinellidae) are disclosed, including the novel compound (−)-(5R, 10R)-subersic acid (1), together with methods of isolation and purification thereof. These compounds are shown to be effective inhibitors of lipoxygenases, specifically human 15-lipoxygenase, and are demonstrated to increase cell viability under ischemic and anoxic conditions, and provide effective treatment for ischemia, congestive heart failure, stroke, and inflammatory conditions generally. Pharmaceutical methods and formulations using (−)-subersic acid (1) and other subersic terpenoids, either derived from natural source such sponge or marine organism, or prepared synthetically, are disclosed. An extract of Suberea sp. (Order: Verongida, Family: Aplysinellidae) is also demonstrated as a lipoxygenase inhibitor.

In other embodiments of the invention, the subject compounds, pharmaceutical compositions and methods may comprise or utilize compounds of the structure:

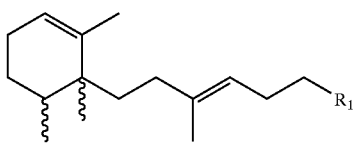

wherein $R_1$ comprises:

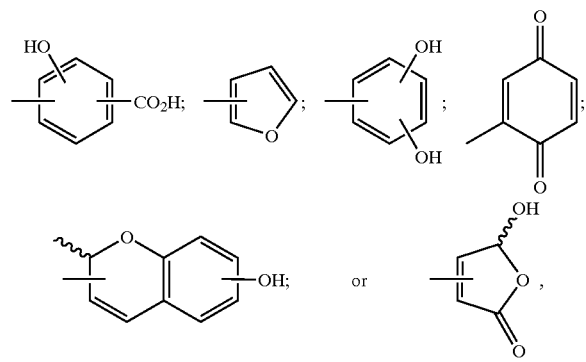

and individual isomers, racemic or non-racemic mixtures of isomers, and pharmaceutically acceptable salts thereof. In specific embodiments, the subject compounds, pharmaceutical compositions and methods may comprise or utilize the novel compound (+)-(5S, 6S)-subersin, also named 3-[4-methyl-6-(1,2,6-trimethyl-cyclohex-2-enyl)-hex-3-enyl]-furan (2):

(2)

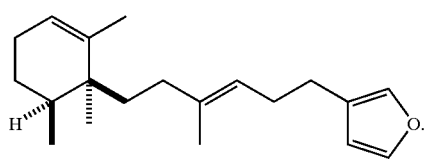

Substantially purified or isolated (+)-(5S, 6S)-subersin (2), together with methods of isolation and purification thereof, are disclosed. (+)-Subersin (2) is shown to be an effective inhibitor of lipoxygenases, specifically human 15-lipoxygenase, is demonstrated to increase cell viability under ischemic and anoxic conditions, and to provide effective treatment for ischemia, congestive heart failure, stroke, and inflammatory conditions generally. Pharmaceutical methods and formulations using (+)-subersin (2) and other subersic terpenoids, either derived from natural source such sponge or marine organism, or prepared synthetically, are disclosed.

In still other embodiments of the invention, the subject compounds, pharmaceutical compositions and methods may comprise or utilize compounds of the structure:

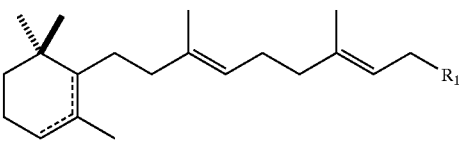

wherein $R_1$ comprises:

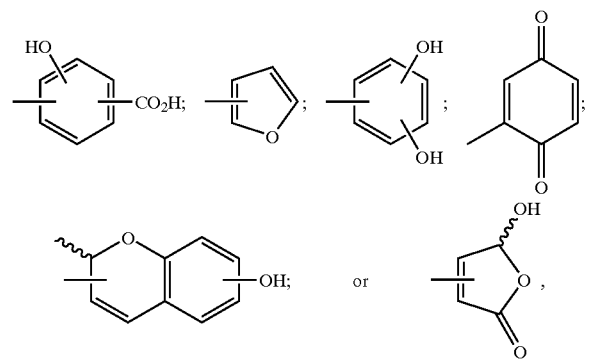

and wherein the 2,6,6-trimethyl cyclohexenyl moiety is unsaturated at either the 1- or 2- position, as well as individual isomers, racemic or non-racemic mixtures of isomers, and pharmaceutically acceptable salts thereof. In specific embodiments, the subject compounds, pharmaceutical compositions and methods may comprise or utilize jaspaquinol, also named 2-[3,7-dimethyl-9-(2,6,6-trimethyl-cyclohex-1-enyl)-nona-2,6-dienyl]-benzene-1,4-diol (3):

(3)

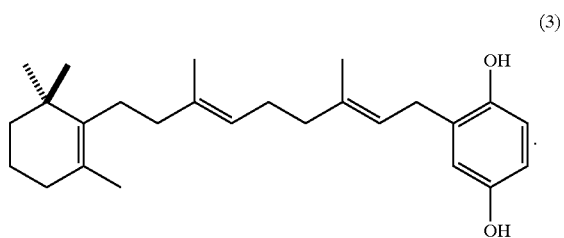

Methods and pharmaceutical compositions for inhibiting lipoxygenases, treatment of lipoxygenase-mediated conditions, prevention of cell damage and promotion of cell viability under ischemic and/or anoxic conditions in mammals and other subjects, and treatment for ischemia, congestive heart failure, stroke, and inflammatory conditions generally, are shown for jaspaquinol (3) and other jaspic terpenoids. These methods and pharmaceutical preparations may comprise the use of one or more jaspic terpenoids derived from *Jaspis johnstoni*, *Jaspis splendens* or other *Jaspis* sp. sponge, or other marine organism or natural source, or which may be synthetically prepared.

In further embodiments of the invention, the subject compounds, pharmaceutical compositions and methods may comprise or utilize compounds of the structure:

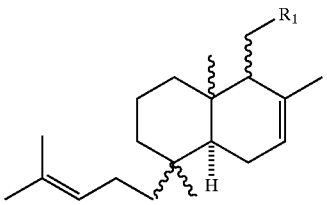

wherein $R_1$ comprises:

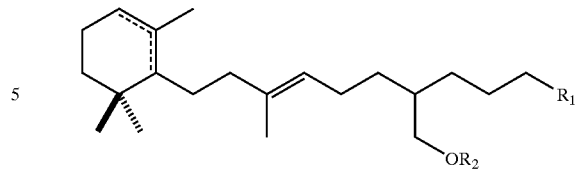

wherein $R_1$ comprises:

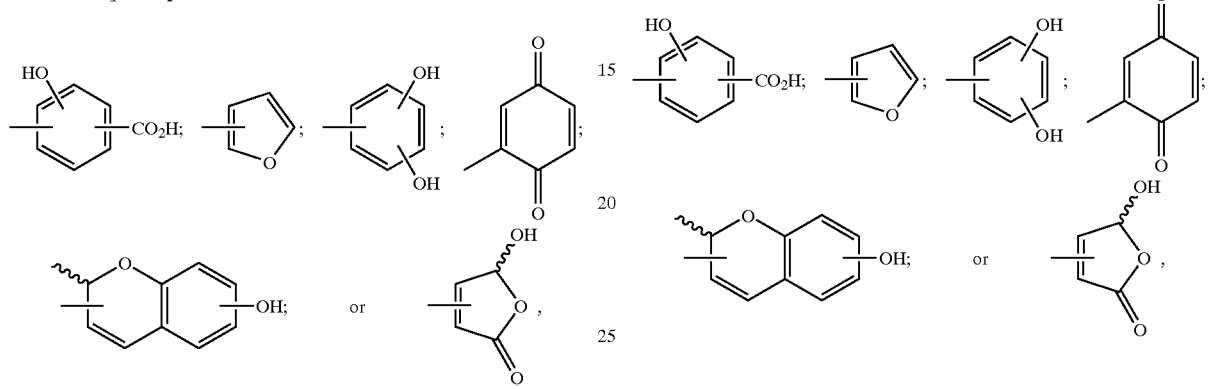

and individual isomers, racemic or non-racemic mixtures of isomers, and pharmaceutically acceptable salts thereof. In specific embodiments the compounds, pharmaceutical compositions and methods may comprise or utilize (−) jaspic acid, also named 4-hydroxy-3-[2,5,8a-trimethyl-5-(4-methyl-pent-3-enyl)-1,4,4a,5,6,7,8,8a-octahydro-naphthalen-1-ylmethyl]-benzoic acid (4):

(4)

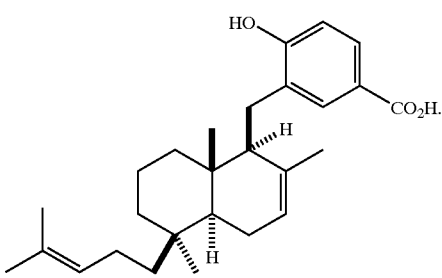

Methods and pharmaceutical compositions for inhibiting lipoxygenases, treatment of lipoxygenase-mediated conditions, prevention of cell damage and promotion of cell viability under ischemic and/or anoxic conditions in mammals and other subjects, and treatment for ischemia, congestive heart failure, stroke, and inflammatory conditions generally, are shown for jaspic acid (4) and other jaspic terpenoids. These methods and pharmaceutical preparations may comprise the use of one or more jaspic terpenoids derived from *Jaspis johnstoni, Jaspis splendens* or other Jaspis sp. sponge, or other marine organism or natural source, or which may be synthetically prepared.

In certain embodiments of the invention, the subject compounds, pharmaceutical compositions and methods may comprise or utilize compounds of the structure:

wherein the 2,6,6-trimethyl cyclohexenyl moiety is unsaturated at either the 1- or 2-position, and wherein $R_2$ comprises: an alkyl group, alkylcarbonyl group, sulfonate, sulfonate salt, or hydrogen, and individual isomers, racemic or non-racemic mixtures of isomers, and pharmaceutically acceptable salts thereof. More specifically, the compounds, pharmaceutical compositions and related methods may comprise or utilize hipposulfate C, also named [2-(3-furan-3-yl-propyl)-6-methyl-8-(2,6,6-trimethyl-cyclohex-2-enyl)-oct-5-enyl] sodium sulfate (5), or its corresponding alcohol igernellin (6), also named 2-(3-furan-3-yl-propyl)-6-methyl-8-(2,6,6-trimethyl-cyclohex-2-enyl)-oct-5-en-1-ol:

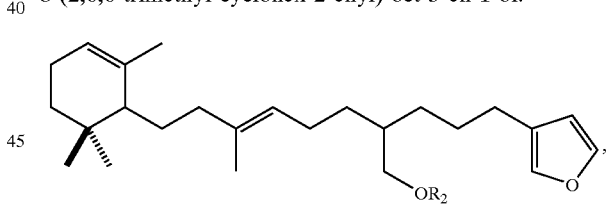

wherein $R_2$ comprises: —SO$_3$Na (5) or —H (6). Methods and pharmaceutical compositions for inhibiting lipoxygenases, treatment of lipoxygenase-mediated conditions, prevention of cell damage and promotion of cell viability under ischemic and/or anoxic conditions in mammals and other subjects, and treatment for ischemia, congestive heart failure, stroke, and inflammatory conditions generally, are shown for hipposulfate C($R_2$=SO$_3$Na) (5) and igernellin ($R_2$=H) (6) as well as other igernellic terpenoids and hippospongic terpenoids, which may be synthetically prepared or derived from a natural source such as Igernella sp., Hippospongia sp., Cocinoderma sp or other sponge family such as Halichondriida, or other marine organism.

In some embodiments, the subject compounds, pharmaceutical compositions and methods may comprise or utilize compounds of the structure:

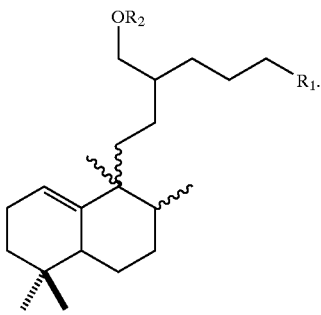

wherein $R_1$ comprises:

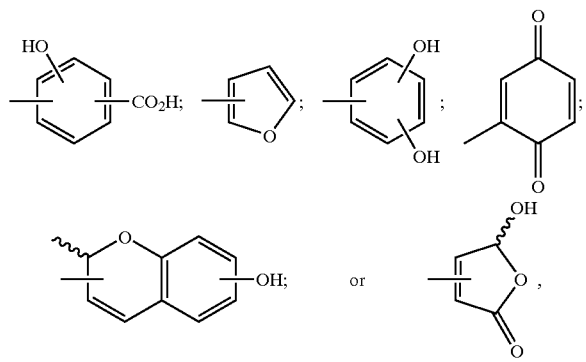

and wherein $R_2$ comprises an alkyl group, alkylcarbonyl group, sulfonate, sulfonate salt, or hydrogen, and individual isomers, racemic or non-racemic mixtures of isomers, and pharmaceutically acceptable salts thereof. More specifically, the subject compounds, pharmaceutical compositions and methods may comprise or utilize halisulfate 7 (7), also named {5-furan-3-yl-2-[2-(1,2,5,5-tetramethyl-1,2,3,4,4a,5,6,7-octahydro-naphthalen-1-yl)-ethyl]- pentyl} sodium sulfate or its corresponding alcohol, 5-furan-3-yl-2-[2-(1,2,5,5-tetramethyl-1,2,3,4,4a,5,6,7-octahydro-naphthalen-1-yl)-ethyl]-pentan-1-ol (8):

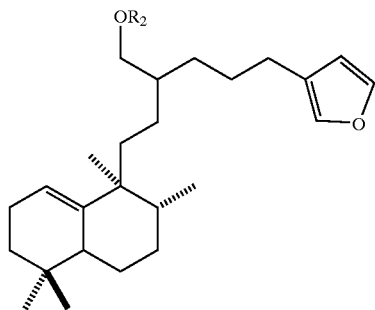

wherein $R_2$ comprises —$SO_3Na$ (7) or —H (8).

Substantially purified or isolated 5-furan-3-yl-2-[2-(1,2,5,5-tetramethyl-1,2,3,4,4a,5,6,7-octahydro-naphthalen-1-yl)-ethyl]-pentan-1-ol (8), together with methods of isolation and purification thereof, are disclosed. Methods and pharmaceutical compositions for inhibiting lipoxygenases, treatment of lipoxygenase-mediated conditions, prevention of cell damage and promotion of cell viability under ischemic and/or anoxic conditions in mammals and other subjects, and treatment for ischemia, congestive heart failure, stroke, and inflammatory conditions generally, are shown for halicondric terpenoids such as Halisulfate 7 (7) and its corresponding alcohol, (8).

In other embodiments, the subject compounds, pharmaceutical compositions and methods may comprise or utilize compounds of the structure:

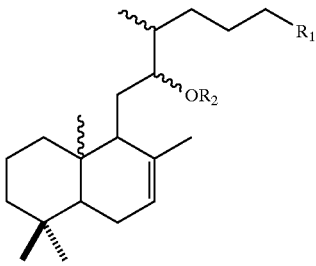

wherein $R_1$ comprises:

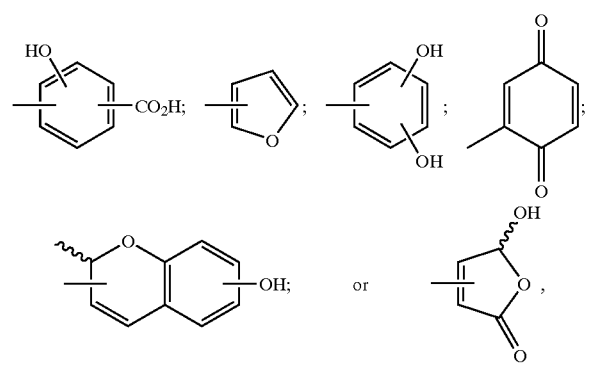

and wherein $R_2$ comprises: an alkyl group, alkylcarbonyl group, sulfonate, sulfonate salt, or hydrogen, and individual isomers, racemic or non-racemic mixtures of isomers, and pharmaceutically acceptable salts thereof. More specifically, the subject compounds, pharmaceutical compositions and related methods may comprise or utilize hipposulfate D ($R_2$=$SO_3Na$) (9), also named 2-[5-hydroxy-4-methyl-6-(2,5,5,8a-tetramethyl-1,4,4a,5,6,7,8,8a-octahydro-naphthalen-1-yl)-hexyl]-2-methyl-2H-chromenyl sodium sulfate, or its corresponding alcohol ($R_2$=H) (10) also named 2-[5-hydroxy-4-methyl-6-(2,5,5,8a-tetramethyl-1,4,4a,5,6,7,8,8a-octahydro-napthalen-1-yl)-hexyl]-2-methyl-2H-chromen-6-ol:

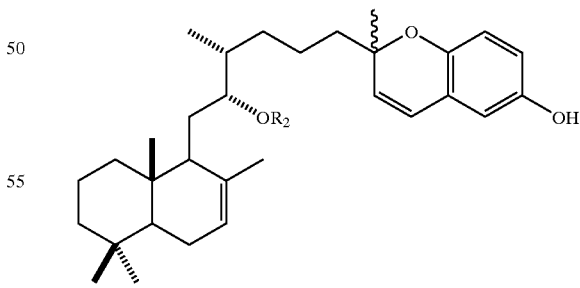

wherein $R_2$ comprises: —$SO_3Na$ (9) or —H (10).

Substantially purified or isolated hipposulfate D (9), together with methods of isolation and purification thereof, are disclosed. Methods and pharmaceutical compositions for inhibiting lipoxygenases, treatment of lipoxygenase-mediated conditions, prevention of cell damage and promotion of cell viability under ischemic and/or anoxic conditions in mammals and other subjects, and treatment for ischemia, congestive heart failure, stroke, and inflammatory conditions generally, are shown for hipposulfate D (9), the alcohol (10), and other hippospongic terpenoids.

In still other embodiments, the subject compounds, pharmaceutical compositions and methods may comprise or utilize compounds of the structure:

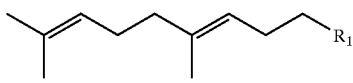

wherein $R_1$ comprises:

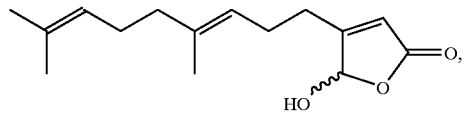

and individual isomers, racemic or non-racemic mixtures of isomers, and pharmaceutically acceptable salts thereof. More specifically, the subject compounds, pharmaceutical compositions and methods may comprise or utilize dictyodendrillin B, also named 4-(4,8-dimethyl-nona-3,7-dienyl)-5-hydroxy-5H-furan-2-one (11):

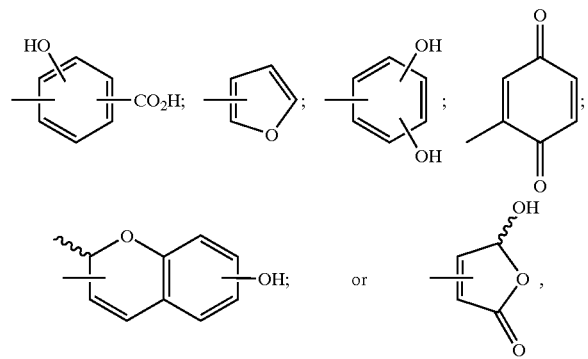

and/or dictyodendrillin C, also named 3-(4,8-dimethyl-nona-3,7-dienyl)-5-hydroxy-5H-furan-2-one (12):

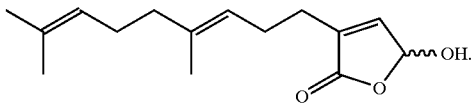

Methods and pharmaceutical compositions for inhibiting lipoxygenases, treatment of lipoxygenase-mediated conditions, prevention of cell damage and promotion of cell viability under ischemic and/or anoxic conditions in mammals and other subjects, and treatment for ischemia, congestive heart failure, stroke, and inflammatory conditions generally, are shown for dictyodendrillin B (11), dictyodendrillin C (12), and other dictyodendric terpenoids.

In certain embodiments, the subject compounds, pharmaceutical compositions and related methods may comprise or utilize compounds of the structure:

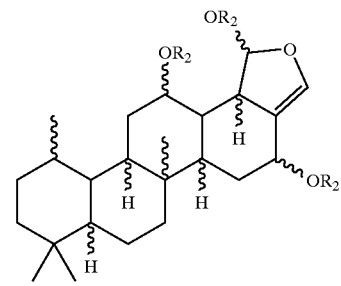

wherein each $R_2$ group individually comprises an alkyl group, alkylcarbonyl group, sulfonate, sulfonate salt, or hydrogen, and individual isomers, racemic or non-racemic mixtures of isomers, and pharmaceutically acceptable salts thereof. More specifically, the subject compounds, pharmaceutical compositions and methods may comprise or utilize heteronemin (13), also named 24,25-epoxy-17(24)-scalarene-12-ol-16,25-diacetate

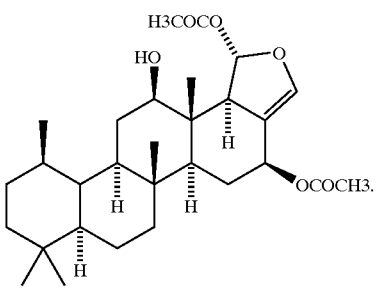

Methods and pharmaceutical compositions for inhibiting lipoxygenases, treatment of lipoxygenase-mediated conditions, prevention of cell damage and promotion of cell viability under isehemic and/or anoxic conditions in mammals and other subjects, and treatment for ischemia, congestive heart failure, stroke, and inflammatory conditions generally, are shown for heteronemin (13) and other heteronemic terpenoids.

The terpenoid compounds above may be used singly or together in various combinations, as well as in various combinations with other known lipoxygenase inhibitors, other bioactive agents, and pharmaceutically acceptable excipients, to provide pharmaceutical preparations and methods in accordance with the invention. The pharmaceutical methods and compositions of the invention are usable for treatment of a variety of lipoxygenase mediated conditions and inflammatory conditions found in mammals and other subjects. The methods and compositions of the invention are also usable for enhancing cell viability and preventing cell damage associated with ischemia, anoxia or hypoxia in various tissues and organs, and for treatment of ischemia, congestive heart failure, stroke, and inflammatory conditions generally in human and other subjects. The subject compounds are also useful for treatment of ischemia, stroke, congestive heart failure, and inflammation that is not associated with lipoxygenase.

The invention also provides novel compounds in isolated or substantially purified form that are useful for treatment of lipoxygenase-mediated conditions and other diseases, disorders or conditions in humans or other mammals. More particularly, the novel compound (–)-(5R, 10R)-subersic acid, also named 4-hydroxy-3-[3-methyl-5-(2,5,5,8a-tetramethyl-3,4,4a,5,6,7,8,8a-octahydro-naphthalen-1-yl)- pent-2-enyl]-benzoic acid (1) is disclosed, together with methods of isolation and purification thereof.

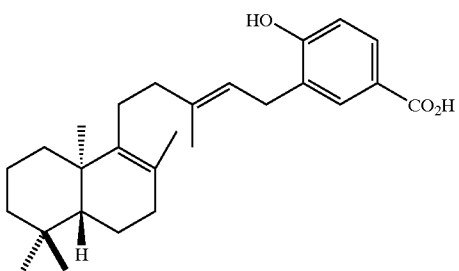

(1)

The novel compound (+)-(5S, 6S)-subersin, also named 3-[4-methyl-6-(1,2,6-trimethyl-cyclohex-2-enyl)-hex-3-enyl]-furan (2) is also disclosed, together with methods of isolation and purification thereof.

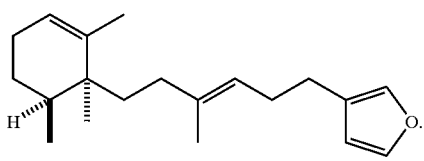

(2)

The novel compounds hipposulfate C, also named [2-(3-furan-3-yl-propyl)-6-methyl-8-(2,6,6-trimethyl-cyclohex-2-enyl)-oct-5-enyl] sodium sulfate (5) and its corresponding sulfonic acid are also disclosed, together with methods of isolation and purification thereof.

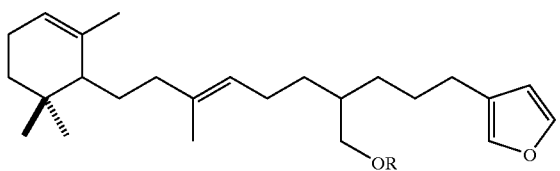

(5)

R = SO$_3$Na or SO$_3$H.

The novel compound (10) 2-[5-hydroxy-4-methyl-6-(2,5,5,8a-tetramethyl-1,4,4a,5,6,7,8,8a-octahydro-naphthalen-1-yl)-hexyl]-2-methyl-2H-chromen-6-ol (10) is also disclosed, together with methods of isolation and purification thereof.

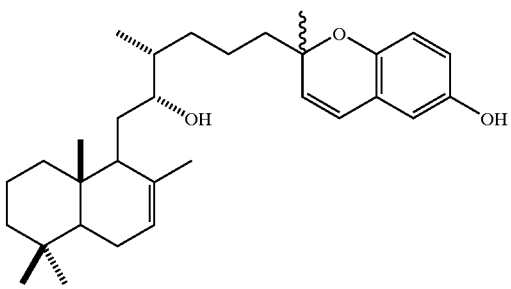

(10)

These and other objects, advantages, and features of the invention will become apparent to those persons skilled in the art upon reading of the details more fully described below.

DEFINITIONS

Unless otherwise stated, the following terms used in the specification and claims have the meanings given below:

"Subersic terpenoid" means any terpene or terpenoid compound found in or derived or isolated from any Suberea sp. sponge, Cacospongia sp. sponge, or any synthetic equivalents or derivatives thereof. Subersic terpenoids include, by way of example, (−)-subersic acid (1), (+)-subersin (2), jaspaquinol (3) and (−) jaspic acid (4). Certain terpene and terpenoid compounds are found in more than one species of sponge, as will be apparent upon review of the following examples. Thus, the compounds jaspaquinol (3) and (−) jaspic acid (4) are also "jaspic terpenoids" as defined below.

"Jaspic terpenoid" means any terpene or terpenoid compound found in or derived or isolated from any Jaspis sp. sponge, or any synthetic equivalents or derivatives thereof. Exemplary jaspic terpenoids include jaspaquinol (3) and (−) jaspic acid (4) (which are also subersic terpenoids as defined above, as jaspaquinol (3) and (−) jaspic acid (4) are isolatable from Suberea sp).

"Igemellic terpenoid" means any terpene or terpenoid compound found in or derived or isolated from any Igernella sp. sponge, or any synthetic equivalents or derivatives thereof. An exemplary igemellic terpenoid is igernellin (6), which is also a hippospongic terpenoid as described below.

"Hippospongic terpenoid" means any terpene or terpenoid compound found in or derived or isolated from any Hippospongia sp. sponge, or any synthetic equivalents or derivatives thereof. Exemplary hippospongic terpenoids include hipposulfate C(R=SO$_3$Na) (5) and its corresponding alcohol igernellin (R=H) (6), hipposulfate D (R=SO$_3$Na) (9) and its corresponding alcohol (R=H) (10), and halisulfate 7 (R=SO$_3$Na) (7) and its corresponding alcohol (R=H) (8).

"Halicondric terpenoid" means any terpene or terpenoid compound found in or derived or isolated from any sponge of the family Halicondriidae, or any synthetic equivalents or derivatives thereof. Exemplary halicondric terpenoids include halisulfates 1–6 (not shown) and halisulfate 7 (7).

"Dictyodendric terpenoid" means any terpene or terpenoid compound found in or derived or isolated from any Dictyodendrilla sp., Cacospongia sp. sponge, or any synthetic equivalents or derivatives thereof. Exemplary dictyodendric terpenoids include dictyodendrillin B (11) and dictyodendrillin C (12).

"Heteronemic terpenoid" means any terpene or terpenoid compound found in or derived or isolated from any Heteronema sp. sponge, or any synthetic equivalents or derivatives thereof. An exemplary heteronemic terpenoid is heteronemin (13).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4methylbicyclo) 2.2.2!oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Pro-drugs" means any compound which releases an active parent drug according to formula (I) in vivo when such prodrug is administered to a mammalian subject. Prodrugs of a compound of formula (I) are prepared by modifying functional groups present in the compound of formula (I) in such a way that the modifications may be cleaved in vivo to release the parent compound. Prodrugs include compounds of formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of formula (I), and the like.

"Treating" or "treatment" of a condition or disease includes: (1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

A "lipoxygenase-mediated condition" means any condition, disorder or disease related to or otherwise associated with a lipoxygenase protein or the inhibition thereof, including, by way of example and without limitation, asthma, atherosclerosis, psoriasis and inflammatory bowel disease, anoxia, hypoxia, or anoxia related conditions such as miocardial infarction, cerebral ischemia, retinal ischemia, myocardial ischemia, post surgical cognitive dysfunction and other ischemias, inflammatory diseases and disorders including diabetes, renal disease, pre-menstrual syndrome, asthma, cardiopulmonary inflammatory disorders, heart failure (including chronic and congestive heart failure), rheumatoid arthritis, osteoarthritis, and muscle fatigue, and neurodegenerative disorders including Alzheimer's, dementia and Parkinson's disease; peripheral neuropathy including spinal chord injury, head injury and surgical trauma; and allograft tissue and organ transplant rejection, and aging and conditions associated with aging.

"Ischemia" means any condition related to or otherwise associated with anoxia, hypoxia or other oxygen-depleted condition, including, for example, local anemia caused by arterial blockage or narrowing in a tissue or organ.

"Lipoxygenase" means any mammalian or non-mammalian lipoxygenase, including 5-, 12-, and 15-lipoxygenases, and particularly human lipoxygenases.

The terms "subject" and "patient" mean a member or members of any mammalian or non-mammalian species that may have a need for the pharmaceutical methods, compositions and treatments described herein.

"Mammal" means a member or members of any mammalian species, and includes, by way of example, canines; felines; equines; bovines; ovines; rodentia, etc. and primates, particularly humans. Animal models, particularly small mammals, e.g. murine, lagomorpha, etc. may be used for experimental investigations.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular terpene or terpenoid compound employed and the effect to be achieved, and the pharmacodynamics associated with each compound in the host.

"Optional" or "optionally" means that the subsequently described event or circumstance may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

DETAILED DESCRIPTION OF THE INVENTION

Before the present compounds and pharmaceutical compositions and methods are described, it is to be understood that this invention is not limited to particular formulations described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a terpenoid" includes a plurality of such terpenoids, and reference to "a lipoxygenase inhibitor" includes reference to one or more lipoxygenase inhibitors and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The invention disclosed herein provides pharmaceutical compositions comprising terpene or terpenoid compounds found in the sponges Suberea sp., Cacospongia sp., Jaspis sp., Igernella sp., Coscinoderma sp., Hippospongia sp., Dictyodendrilla sp., Heteronema sp., or of the family Halichondriidae, and other sponge or natural sources, or synthetic derivatives thereof, which exhibit lipoxygenase inhibition activity or are efficacious in the treatment of lipoxygenase-mediated conditions, or are effective at promoting or improving cell viability or preventing cell damage in various tissues or organs under ischemic, anoxic or hypoxic conditions.

The invention also provides methods for inhibiting lipoxygenase comprising contacting or exposing a lipoxygenase to an effective amount of one or more of the subject compounds. The invention further provides methods for treating a subject suffering from a lipoxygenase-mediated condition comprising administering to the subject a therapeutically effective amount of one or more of the subject compounds.

The invention additionally provides methods for preventing cell damage and/or increasing cell viability in various tissues and organs under ischemic, anoxic or hypoxic conditions comprising contacting or exposing cells to an effective amount of one or more of the subject compounds. The invention further provides methods for treating a subject suffering from ischemia, stroke, inflammatory condition, and anoxia or hypoxia in a tissue or organ, comprising administering to the subject a therapeutically effective amount of one or more of the subject compounds.

By way of example, and not of limitation, the subject compounds may be of synthetic origin, or derived or isolated from the aforementioned sponges, or derived or isolated from other natural source, or prepared synthetically. The subject compounds may comprise, by way of example, one or more compounds selected from the group of:

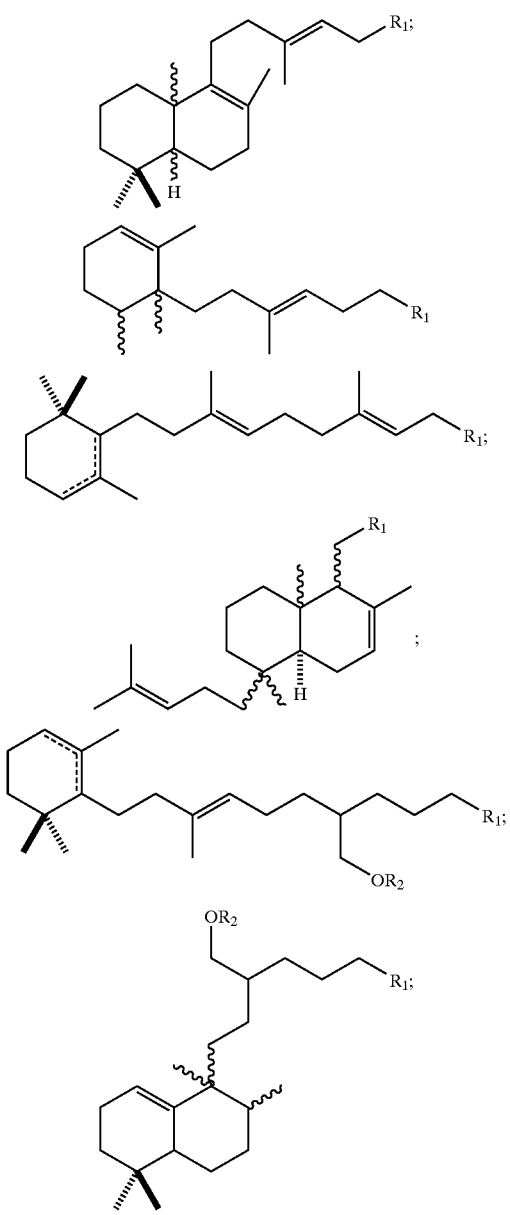

-continued

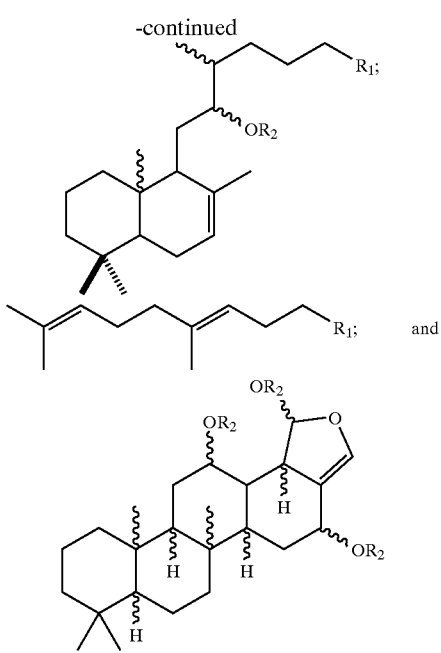

wherein $R_1$, comprises:

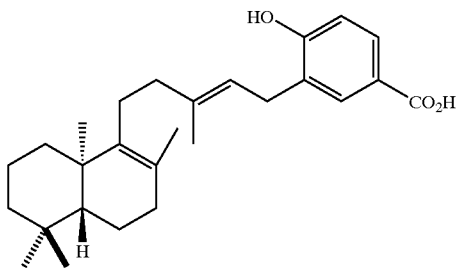

or

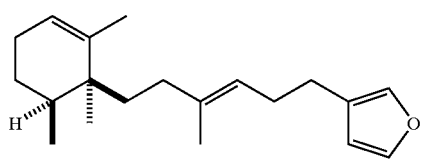

and wherein $R_2$ comprises an alkyl group, alkylcarbonyl group, sulfonate, sulfonate salt, or hydrogen.

More specifically, the subject compounds may comprise one or more compounds selected from the group of:

(1)

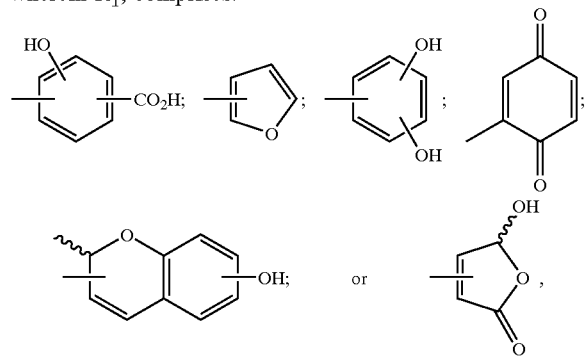

(−)-(5R, 10R)-subersic acid (1), also named 4-hydroxy-3-[3-methyl-5-(2,5,5,8a-tetramethyl-3,4,4a,5,6,7,8,8a-octahydro-naphthalen-1-yl)-pent-2-enyl]-benzoic acid;

(2)

(+)-(5S, 6S)-subersin (2), also named 3-[4-methyl-6-(1,2,6-trimethyl-cyclohex-2-enyl)-hex-3-enyl]-furan;

(3)

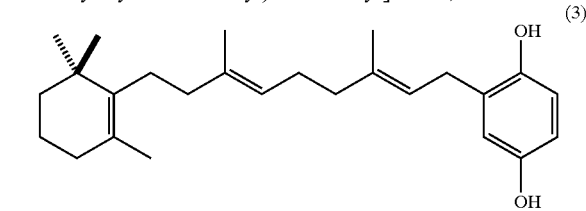

jaspaquinol (3), also named 2-[3,7-dimethyl-9-(2,6,6-trimethyl-cyclohex-1-enyl)-nona-2,6-dienyl]-benzene-1,4-diol;

(4)

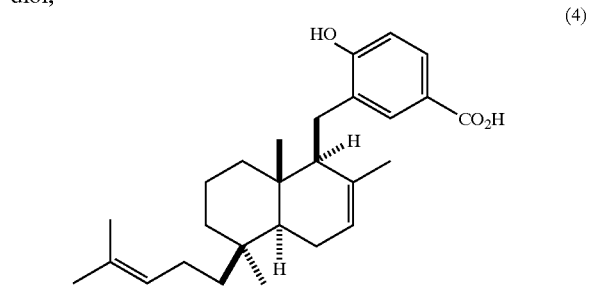

(−) jaspic acid (4), also named 4-hydroxy-3-[2,5,8a-trimethyl-5-(4-methyl-pent-3-enyl)-1,4,4a,5,6,7,8,8a-octahydro-naphthalen-1-ylmethyl]-benzoic acid;

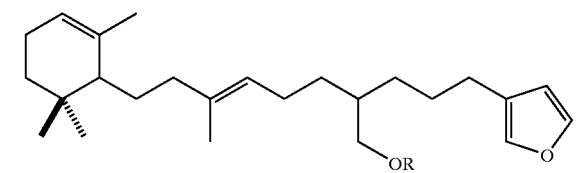

R = SO$_3$Na = (5)
R = H         (6)

hipposulfate C(R SO$_3$Na) (5), also named [2-(3-furan-3-yl-propyl)-6-methyl-8-(2,6,6-trimethyl-cyclohex-2-enyl)-oct-5-enyl] sodium sulfate or its corresponding alcohol igernellin (R═H) (6), also named 2-(3-furan-3-yl-propyl)-6-methyl-8-(2,6,6-trimethyl-cyclohex-2-enyl)-oct-5-en-1-ol;

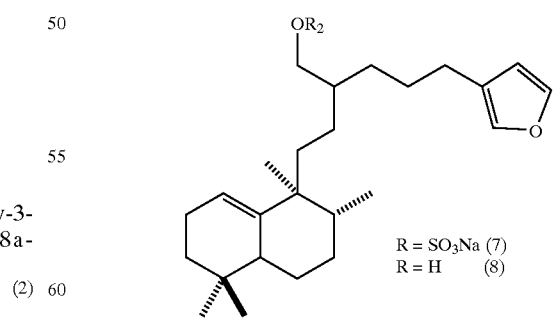

R = SO$_3$Na (7)
R = H        (8)

halisulfate 7 (R═SO$_3$Na) (7), also named {5-furan-3-yl-2-[2-(1,2,5,5-tetramethyl-1,2,3,4,4a,5,6,7-octahydro-naphthalen-1-yl)-ethyl]-pentyl} sodium sulfate or its corresponding alcohol (R═H) (8), also named 5-furan-3-yl-2-

[2-(1,2,5,5-tetramethyl-1,2,3,4,4a,5,6,7-octahydro-naphthalen-1-yl)-ethyl]-pentan-1-ol;

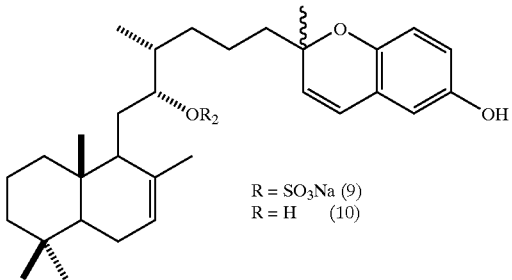

R = SO₃Na (9)
R = H (10)

hipposulfate D (R=SO₃Na) (9), also named 2-[5-hydroxy-4-methyl-6-(2,5,5,8a-tetramethyl-1,4,4a,5,6,7,8,8a-octahydro-naphthalen-1-yl)-hexyl]-2-methyl-2H-chromenyl sodium sulfate, or its corresponding alcohol (R=H) (10), also named 2-[5-hydroxy-4-methyl-6-(2,5,5,8a-tetramethyl-1,4,4a,5,6,7,8,8a-octahydro-naphthalen-1-yl)-hexyl]-2-methyl-2H-chromen-6-ol;

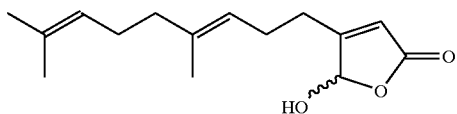

dictyodendrillin B (11), also named 4-(4,8-dimethyl-nona-3,7-dienyl)-5-hydroxy-5H-furan-2-one;

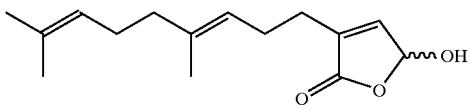

dictyodendrillin C (12), also named 3-(4,8-dimethyl-nona-3,7-dienyl)-5-hydroxy-5H-furan-2-one and

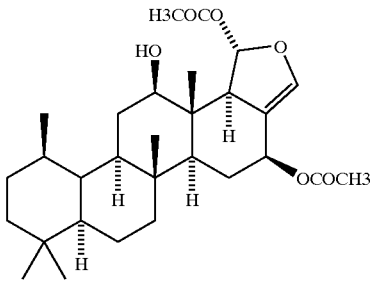

heteronemin (13), also named 24,25-epoxy-17(24)-scalarene-12-ol-16,25-diacetate

The cellular and molecular mechanisms associated with lipoxygenase-mediated conditions, such as those that lead to neuronal damage and inflammation associated with various types of brain ischemia, can be carried out using in vitro model systems, such as primary cell cultures, that retain the metabolic characteristics of neurons in vivo. The use of such cell-based models has led to advances in identification of biochemical mechanisms leading to neuronal death in conditions such as anoxia, hypoglycemia, excitotoxicity, and exposure to reactive oxygen species. Neuronal cell lines such as the pheochromocytoma cell line, PC12, are also useful models for studying the effects of oxidative stress on the structure: and function of neuron-specific proteins that are expressed in the cell lines. As many neuronal cell lines do not express all the properties of genuine neurons, primary neuronal cultures are now widely used as in vitro models in which to discern the processes that occur in intact brain.

In vitro models of ischemia can provide oxygen and glucose deprivation that mimic in vivo conditions, for example, by placing neuronal cultures into large anaerobic or hypoxic chambers and exchanging culture medium with oxygen-free and defined ionic composition media. The toxic overstimulation of neuronal glutamate receptors, especially N-methyl-D-aspartate (NMDA) receptors, contribute to hypoxic-ischemic neuronal injury (Choi, D. M., Neuron 1988, 1: 623–634), ischemic induction of reactive oxygen species (ROS) (Watson, B. D., et al., Ann NY Acad. Sci. 1988, 59: 269–281), excessive calcium influx (Grotta, J. C., Stroke 1988, 19: 447–454), arachidonic acid increase (Siesjo, B. K., J. Cereb. Blood Flow Metab. 1981, 1: 155–186), and DNA damage (MacManus, J. P., et al., Neurosci. Lett., 1993, 164: 89–92) causing a cascade of neurodegeneration.

Primary embryonic hippocampal neuronal cells are widely recognized as models of neuronal function. The hippocampus is a source of a relatively homogenous population of neurons with well-characterized properties typical of central nervous system (CNS) neurons in general. Pyramidal neurons, the principal cell type in the hippocampus, have been estimated to account for 85% to 90% of the total neuronal population (Banker and Goslin, Culturing Nerve Cells, 2$^{nd}$ edition 1998, The MIT Press, Cambridge, Mass.). The hippocampus also exhibits a remarkable capacity for activity-dependent changes in synaptic function, such as long-term potentiation (Hawkins et al, Ann. Rev Neurosci. 1993, 16, 625–665).

In experiments carried out in support of the present invention and shown in the examples below, anoxia/ischemia was induced in primary cultures of hippocampal neuronal cells, and the subject terpenoid compounds of the invention were tested for their ability to prevent cell death due to ischemia. Briefly, primary cultures of hippocampal neurons may be used to test compounds for activity in neuronal protection. Cultures are typically prepared from 18- to 19-day fetal rats. At this age, the generation of pyramidal neurons, which begins in the rat at about E15, is essentially complete. The brain tissue at this stage is relatively easy to dissociate, the meninges are removed readily, and the number of glial cells still is relatively modest (Park et al., J Neurochem 2000, 74(1), 114–124).

In order to determine activity, each compound was assessed for its ability to protect cells against one or more standard stressors, including hypoxia, as detailed in the Examples. Compounds that are neuroprotective in such an in vitro cell systems are usable in appropriate in vivo animal models.

Similarly, primary cultures of myocytes were used to test the subject compounds in vitro for ability to provide protection against heart damage, such as myocardial ischemia or congestive heart failure. Such cells are typically used to study molecular models of myocardial ischemia (Webster et al., J. Mol. Cell Cardiol. 1995, 27, 453–458; Camilleri et al., Cell Biol. & Toxicol. 1997, 13, 435–444; Bielawska et al., Am. J. Pathol. 1997, 151:1257–1263) and therefore can be used to screen for myoprotective compounds, as described herein. Exemplary stressor assays for this purpose are provided in the examples below. For example, cardiomyocytes in culture exhibit contractile ("beating") activity; each cardiomyocyte contraction is associated with a rise in intracellular calcium termed a "calcium transient". These calcium transients can be measured using Fluo-4, a fluorescent dye which exhibits large fluorescence intensity increases on binding calcium. This assay is cell-based and tests the ability of potential cytoprotectant molecules to guard against ischemic damage and allow the cells to maintain their contractile function.

The subject compounds have been further evaluated and validated as pharmacologically efficacious using in vitro assays based on a variety of different cell lines known in the art, as well in vivo via appropriate animal or whole organ assays, such as the isolated heart model of cardiac function, the rat air pouch model for inflammation, the rat middle-cerebral artery occlusion (MCAO) stroke model, and others. Similarly, the subject compounds can be further validated in additional animal models (e.g., diabetes, renal failure, asthma, muscle fatigue, inflammation), such as are well known in the art.

Utility

The subject compounds are usable for administration to subjects exhibiting or suffering from lipoxygenase-mediated conditions, diseases or disorders, including any condition, disease or disorder associated with lipoxygenase inhibition and, more specifically in the case of human subjects, with human 15-lipoxygenase inhibition. The subject compounds are usable for administration to subjects exhibiting or suffering from ischemia, hypoxia or anoxia-related conditions. The aforementioned conditions, diseases and disorders include, without limitation, asthma, atherosclerosis, psoriasis and inflammatory bowel disease, anoxia, hypoxia, or anoxia related conditions such as miocardial infarction and cerebral ischemia (stroke), other ischemias, and inflammatory conditions generally. Inflammatory diseases and disorders include without limitation diabetes, renal disease, premenstrual syndrome, asthma, cardiopulmonary inflammatory disorders, heart failure (including chronic and congestive heart failure), rheumatoid arthritis, osteoarthritis, and muscle fatigue. The compounds are also usable for administration to subjects exhibiting conditions characterized by oxidative stress including without limitation, ischemia including stroke, congestive heart failure, cerebral ischemia, retinal ischemia, myocardial ischemia, myocardia infarction and post surgical cognitive dysfunction; neurodegenerative disorders including Alzheimer's, dementia and Parkinson's disease; peripheral neuropathy including spinal chord injury, head injury and surgical trauma; and for the preservation of allograft tissue or organ for transplantation. Various other diseases, conditions or disorders treatable using the subject compounds, pharmaceutical formulations thereof, and related methods, will suggest themselves to those skilled in the art and are also considered to be within the scope of this disclosure.

Pharmaceutical Preparations

Also provided by the invention are pharmaceutical preparations of the subject compounds. The subject compounds can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. The formulations may be designed for administration via a number of different routes, including oral, buccal, rectal, parenteral, intraperitoneal, intradermal, transdermal, intracheal, etc., administration.

In pharmaceutical dosage forms, the subject compounds of the invention may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the subject compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The subject compounds of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds of the invention can be utilized in aerosol formulation to be administered via inhalation. The compounds of the present invention can be formulated into pressurized acceptable propellants such as dichlorodifluoromethane, propane, nitrogen and the like.

Furthermore, the subject compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

Depending on the patient and condition being treated and on the administration route, the subject compounds may be administered in dosages of, for example, 0.1 □g to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be ten times the injection dose. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

For use in the subject methods, the subject compounds may be formulated with other pharmaceutically active agents, including other lipoxygenase-inhibiting agents.

Pharmaceutically acceptable excipients usable with the invention, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Kits with unit doses of the subject compounds, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General Spectroscopic Experimental Procedures

NMR spectra were recorded in $CDCl_3$ and $CD_3OD$ solutions at 500 or 125.7 MHz for $^1H$ and $^{13}C$ respectively. Optical rotation was measured using a JASCO DIP-370 digital polarimeter. UV data were obtained with a Hewlett-Packard 8452 Diode Array Spectrophotometer. ESIMS spectra were acquired using a VG Quatto II. HRMS were obtained with a PE Biosystems Mariner and JEOL JMS-AX505HA mass spectrometers.

Example 1

Taxonomic Identification of Suberea sp.

Sponge specimens of Suberea sp. (Order: Verongida, Family: Aplysinellidae, UCSC Collection No. 97243) were obtained by SCUBA at a depth of approximately 20 meters in the Madang region of Papua New Guinea. The specimens were massive globular sponges that dark gray in external color and tan-colored internally. The sponge surfaces were conulose and had a dense, rubbery consistency which became very hard in dry specimens. The skeleton consisted only of fibers, typical of Verongids, with amber, concentrically layered fibers of 250–300 µm diameter, with a strong organic pith of 40–50 µm in diameter. The nature of the fibers, with both pith and bark well represented, indicated genus Suberia (Bergquist, *Memoirs of the Queensland Museum* 1995, 38, 1–51).

Example 2

Extraction and Isolation of (–)-Subersic Acid (1), (+)-Subersin (2), Jaspaquinol (3) and (–) Jaspic Acid (4) from Suberea sp.

Sponge samples were preserved by immersion in a 1:1 EtOH/sea water solution. This solution was decanted after 24 hr and discarded. The damp sponge samples were extracted with 100% MeOH to give a crude oil which was partitioned between several solvents in a conventional manner. The hexane and methylene chloride fractions were further purified on Biotage Si gel columns using methylene chloride and EtOAc/Hexane (50/50) respectively to give five fractions of each. These fractions were further purified by reverse phase gradient HPLC to give (–)-subersic acid (1) (0.01% dry wt of sponge), (+)-subersin (2) (0.02% dry weight of sponge, jaspaquinol (3) (0.01% dry wt of sponge) and (–)-jaspic acid (4) (0.025% wt dry sponge). The properties of jaspaquinol (3) and (–)-jaspic acid (4) isolated from Suberea sp. were the same as described in Example 5 below.

Example 3

Characterization of (–)-subersic Acid (1)

Analysis (HRFABMS) of the fraction leading to (1) provided a molecular formula $C_{27}H_{38}O_3$. The HRTOFMS data for (1) were identical to that of (–)-jaspic acid (4) (Murray et al., *J. Org. Chem.* 1997, 62, 5638–5641), with $[M-H]^-$ m/z=409.2743 (Δ0.0 mmu of calcd.). The NMR data however were dissimilar, showing that (1) and (4) were structural isomers. The DEPT-135 $^{13}C$ NMR data gave $5CH_3+7CH_2+7CH+8C$, totaling $C_{27}H_{36}$, making it evident that two OH residues were present, with one as an aromatic ring OH (159.8, s), and the other as part of a carboxylic acid (δ 171.7, s). There were striking similarities in the $^{13}C$ NMR data between (–)-subersic acid (1) and (–)-jaspic acid (4) that allowed the two substructure:s (1a) and (1b) to be determined.

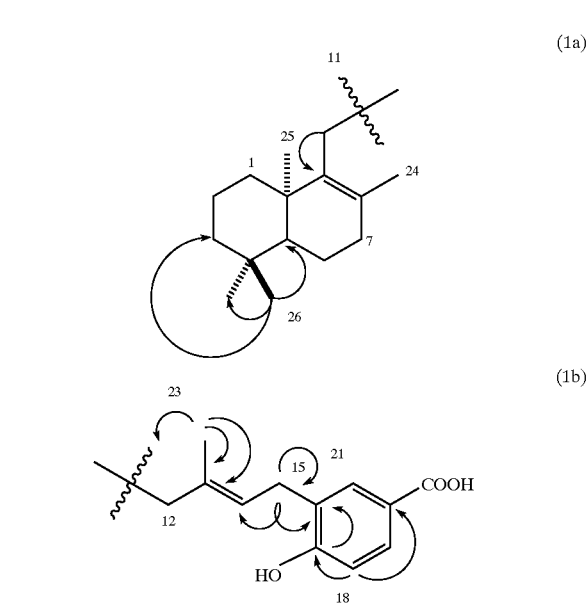

The 4-hydroxybenzoic acid moiety of 1b had identical shifts to those of 4 between C15 through C22 which were verified by gHMBC data (shown in FIG. 1): H18 (δ 6.86) to C16 and C20; H15 (δ 3.42) to C13, C14, C16, C17 and C21;

H21 &/or H19 (δ 7.91) to C17, C16, and C15; and H23 (δ 1.83) to C12, C13, C14. The $^{13}$C NMR of the bicyclic $C_1$–$C_{11}$ portion of (1a) was identical to that of published data for this well-known ring system (Capon et al., *J. Nat. Prod.* 1998, 61, 525–528; Butler et al., *Aust. J. Chem.*, 1992, 45, 1705–1743). The side chain attachment was identified from the gHMBC correlations H11 (δ 2.14) to C8, C9, and C12, with the latter correlation to C12 supporting the proposed interconnection of substructure:s (1a) and (1b). The E geometry of position $\Delta^{13/14}$ could be deduced from the upfield $^{13}$C NMR shift of methyl C23 (δ 16.7).

Assignment of the stereochemistry was addressed for (2) (11 by a detailed comparison of its molecular rotation to that of the same ring system, previously determined by Capon et al., supra. The measured molar rotation ([Φ]=−189) of (−)-subersic acid is comparable with the [Φ] =−191 reported by Capon et al. for substructure (14);

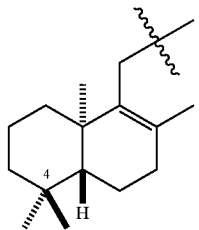

(14)

This analysis indicates 5R, 10R stereochemistry for (−)-(5R, 10R)-subersic acid (1): yellow oil; 12 mg; [α]$_D$ −46° (c 0.5, CHCl$_3$); m/z=409.2743 [M−H]$^-$ (Δ0.0 mmu of calcd. for $C_{27}H_{38}O_3$); $^1$H NMR (500 MHz, CDCl$_3$) δ (ppm) 7.91 (s, 2H, H21 & H19), 6.86 (d, J=10 Hz H18), 5.36 (t, J=5 Hz, H14), 3.42 (d, J=10 Hz, H$_3$, H15), 2.14 (m, 2H, H11), 2.12 (m, 2H, H12), 2.09 (m, 2H, H7), 1.83 (m, H1), 1.83 (s, H$_3$, H23), 1.62 (m, 4H, H6 & H23), 1.58 (s, H$_3$, H24), 1.17 (m, H3'), 1.14 (m, 2H H1' & H5), 0.95 (s, H$_3$, H25), 0.89 (s, H$_3$, H26), 0.84 (s, H$_3$, H27). $^{13}$C NMR (125 MHz, CDCl$_3$) δ (ppm) 171.7 (s, C22), 159.8 (s, C17), 141.0 (s, C13), 132.9 (d, C21), 130.8 (d, C19), 127.0 (s, C16), 126.3 (s, C8), 121.9 (s, C20), 120.3 (d, C14), 116.0 (d, C18) 5.21 (s, C5), 42.1 (t, C3), 40.7 (t, C12), 39.3 (s, C10), 37.3 (t, C1) 33.9 (t, C7), 33.6 (s, C4), 33.6 (q, C26), 29.9 (t, C15), 27.3 (t, C11), 21.9 (q, C27), 20.4 (q, C25), 19.8 (q, G24), 19.3 (t, C2), 19.3 (t, C6), 16.7 (q, C23).

Example 4

Characterization of (+)-subersin (2)

The characterization of (+)-subersin (2) commenced with establishing the molecular formula of $C_{20}H_{30}O$ (HRFABMS). The formula was supported by data including: positive ion HREIMS m/z 286.2267 [M]$^+$ (Δ 3.0 mmu of calcd.), and the DEPT-135 $^{13}$C NMR carbon types, 4CH$_3$+ 6CH$_2$+6CH+4C, for a count of $C_{20}H_{30}$. A furan moiety was proposed since heteroatom hydrogens were lacking and characteristic $^{13}$C NMR shifts could be located (δ 142.7, d, C15; 139.1, d, C16; 125.1, s, C13; 111.3, d, C14). There were also two double bonds (δ 139.6, s, C1; 122.1, d, C2; 137.2, s, C9; 123.3, d, C10). The aforementioned features accounted for five of the six degrees of unsaturation, indicating that a carbocyclic ring was present.

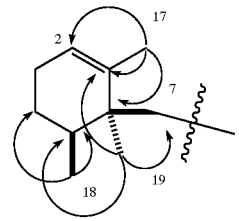

2a

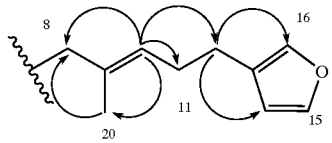

2b

The substructure:s (2a) and (2b) were assembled as follows. A set of $^1$H-$^1$H COSY correlations revealed the spin systems H2-H3-H4-H5-H$_3$18, H10-H11-H12, H14-H15. Additional important data came from a series of Me-based $^1$H-$^{13}$C gHMBC correlations (FIG. 1) H$_3$17 (δ 1.63) to C1, C2, and C6; H$_3$18 (δ 0.94) to C4, C5, and C6; H$_3$19 (δ 1.03) to C1, C5, C6, and C7; H$_3$20 (δ 1.59) to C8; and the other $^1$H-$^{13}$C gHMBC correlations shown in FIG. 1. The substructures (2a) and (2b) could be interconnected using the $^1$H-$^{13}$C gHMBC correlation from H7' (δ 1.34) to C8. Next, the relative stereochemistry was determined through 1D-nOe correlations from H$_3$19 (δ 1.03) to H5 and from H$_3$18 (δ 0.94) to H7. As expected, the $^{13}$C NMR shifts of trans methyls 18 and 19 agree with those of a sponge-derived sesterterpene containing substructure: (2a):

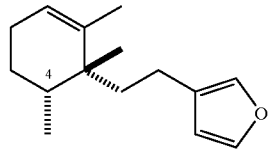

(15)

The 4R, 5R absolute stereochemistry known for (−)-microcionin-2 (15), which has been assigned by total synthesis (Potvin et al., *Tetrahedron Asymmetry*, 1986, 7, 2821–2824), was used to delineate 5S, 6S stereochemistry for (2), given that the molar rotation for (2) ([Φ]=+10), is similar in magnitude but of opposite sign, to that of (15) [Φ]=−27) (Cimino et al., *Tetrahedron Lett.* 1975, 43, 3723–3726).

(+)-(5S, 6S)-Subersin (2): yellow oil; 24mg; [α]$_D$ +30° (c 2.6, CHCl$_3$); HREIMS m/z 286.2267 [M]$^+$ (δ 3.0 mmu of calcd. for $C_{20}H_{30}O$) $^1$HNMR (500 MHz, CDCl$_3$) δ (ppm) 7.34 (s, H15), 7.22 (d, J=0.5 Hz H16), 6.28 (s, H14), 5.40 (s, H2), 5.17 (t, J=7.5 Hz, H10) 2.45 (t, J=8 Hz, 2H, H12), 2.24 (q, J=8 Hz, 2H, H11), 1.97 (m, H8), 1.96 (m, 2H, H3), 1.89 (M, H8'), 1.63 (s, H3, H17), 1.60 (m, H4), 1.59 (s, H$_3$, H20), 1.57 (m, H5), 1.47 (m, H7), 1.43 (m, H4'), 1.34, (m, H7'), 1.03 (s, H$_3$, H19), 0.94 (d, J=8 Hz, H$_3$, H18). $^{13}$C NMR (125 MHz, CDCl$_3$) δ (ppm) 142.7 (d, C15), 139.6 (s, C1), 139.1 (d, C16), 137.2 (s, C9), 125.1 (s, C13), 123.3 (d, C10), 122.1 (d, C2), 111.3 (d, C14), 39.8 (s, C6), 37.8 (d, C5), 35.8 (t, C8), 34.7 (t, C7), 28.6 (t, C11), 27.5 (t, C4), 26.6 (q, C19), 25.1 (t, C12), 24.1 (t, C3), 19.7 (q, C17), 16.3 (q, C20), 16.0 (q, C18).

Example 5

Extraction and Isolation of Jaspaquinol (3) and (−) Jaspic Acid (4) from Jaspis sp.

Jaspis cf. johstoni were collected via SCUBA off the Madang region of Papua New Guinea as described by Murray et al., *J. Org. Chem.* 1997, 62, 5638–5641. Taxonomic identification of the Jaspis sp. sponges was carried out as described by Sanders et al., *Memoirs of the Queensland Museum* 1999, 44, 525–532. Samples of such sponge are preserved as UC Santa Cruz Collection No. 96117. Extraction and isolation was carried out as described by Murray et al. supra. Briefly, sponges were soaked in 100% MeOH, and the resultant crude oil was successively partitioned between equal volumes of aqueous MeOH, percent adjusted to produce a biphasic solution, and hexane followed by methylene chloride. The remaining water solubles were extracted with sec-BuOH. The methylene chloride fraction was subjected to Sephadex LH-20 gel filtration chromatography in methylene chloride/MeOH (30:70) to give six fractions. The fourth fraction was subjected to reverse phase HPLC to provide jaspaquinol (3) and (−)-jaspic acid (4).

The jaspaquinol (3) (0.02% dry wt of sponge) was a yellow oil showing UV [λ] 217, 290; IR (film) 330, 2927, 1652 cm$^{-1}$. LRFABMS, positive ion, m/z (relative intensity %) 381 [M−H]$^+$ (10), 275 (6), 243 (88), 203 (10), 137 (100); HRFABMS 381.2795 [M−H]$^+$=C$_{26}$H$_{37}$O$_2$ requires 381.2794. The (−)-jaspic acid (4) (0.03% dry wt of sponge) showed UV [λ] 216, 258, 290; IR (film) 3300, 2923, 1685, 1603, 1275 cm$^{-1}$. LRFABMS, positive ion, m/z (relative intensity %) 409 [M−H]$^+$ (48), 275 (27, 215 (28), 145 (71), 119 (100); HRFABMS 409.2743 [M−H]$^+$ =C$_{27}$H$_{37}$O$_3$ requires 409.2743. $^1$H and $^{13}$C NMR were substantially identical to the results reported by Murray et al., supra. The properties of jaspaquinol (3) and (−)-jaspic acid (4) isolated from Jaspis sp. were the identical to those isolated from Suberea sp. in Example 1.

Example 6

Extraction, Isolation and Identification of Hipposulfate C (5) and the Corresponding Alcohol Igernellin (6)

Hippospongia sp. (order Dictyoceratida, family Spongiidae (UCSC collection number 97220) was collected off Papua New Guinea at a depth of approximately 15 meters. The sponge was described as massive oblong to fan in shape with a compressible consistency. The color was black in the live specimens and dark brown to black when dry. Ectosomal matter was non-specialized, but foreign material was concentrated, whereas the choanosome showed whorls of wool-like secondary reticle (fibers 15–30 μm). There were no spicules in the specimens.

Specimens were extracted with MeOH, and step gradient column chromatography (methylene chloride/methanol) of the extract gave four fractions which were further purified by RPHPLC to give Hipposulfate C (5) as a colorless oil, [α]$_D$=−68° (c 2.3 MeOH); $^1$H NMR and $^{13}$C NMR are shown in Table 1; HRFABMS m/z [M−Na]$^-$=451.2508 (calcd for C$_{25}$H$_{39}$O$_5$S, 451.2518). The corresponding sulfonic acid was also prepared by treatment of (5) with dilute HCl.

TABLE 1

NMR Data for Hipposulfate C (5) and Corresponding Alcohol Igernellin (6).[a]

| | hipposulfate C (5) | | alcohol (6) | |
|---|---|---|---|---|
| atom | δ$_C$[b] (mult) | δ$_H$[c] (mult, JHz) | δ$_C$[c] (mult) | δ$_H$[c] (mult, JHz) |
| 1 | 119.4 (d) | 5.22 (bs) | 119.9 (d) | 5.29 (bs) |
| 2 | 25.4 (t) | 1.41 (m) | 25.2 (t) | 1.71 (m) |
| 3 | 31.5 (t) | 1.40 (m) | 31.7 (t) | 1.59 (m) |
| 4 | 32.1 (s) | | 32.4 (s) | |
| 5 | 47.0 (d) | 1.43 (m) | 48.1 (d) | 1.31 (m) |
| 6 | 137.0 (s) | | 136.5 (s) | |
| 7 | 30.3 (s) | 1.31 (m) | 30.0 (t) | 1.50 (m) |
| 8 | 40.3 (t) | 1.94 (m) | 40.7 (t) | 2.01 (m) |
| 9 | 135.4 (s) | | 136.0 (s) | |
| 10 | 124.2 (d) | 5.06 (t, 5) | 124.4 (d) | 5.12 (t, 10) |
| 11 | 25.4 (t) | 1.99 (m) | 25.3 (t) | 2.00 (m) |
| 12 | 31.2 (t) | 1.40 (m) | 31.1 (t) | 1.40 (m) |
| 13 | 37.0 (d) | 1.64 (m) | 40.1 (d) | 1.45 (m) |
| 14 | 30.8 (t) | 1.40 (m) | 30.6 (t) | 1.10 (m) |
| 15 | 26.9 (t) | 1.59 (m) | 27.4 (t) | 1.56 (m) |
| 16 | 24.4 (t) | 2.34 (t, 10) | 23.6 (t) | 2.43 (t, 7) |
| 17 | 124.2 (s) | | 125.0 (s) | |
| 18 | 110.9 (d) | 6.25 (s) | 111.0 (d) | 6.27 (s) |
| 19 | 142.3 (d) | 7.32 (s) | 142.8 (d) | 7.36 (s) |
| 20 | 26.5 (q) | 0.82 (s) | 27.5 (q) | 0.87 (s) |
| 21 | 26.5 (q) | 0.88 (s) | 27.7 (q) | 0.96 (s) |
| 22 | 22.3 (q) | 1.60 (s) | 23.2 (q) | 1.68 (s) |
| 23 | 15.1 (q) | 1.55 (s) | 16.2 (q) | 1.55 (s) |
| 24 | 69.8 (t) | 3.88 (t, 15) | 65.6 (t) | 3.57 (d, 5) |
| 25 | 137 (d) | 7.20 (s) | 138.9 (d) | 7.28 (s) |

[a]Spectra were recorded at 125 MHz for $^{13}$C and 500 MHz for $^1$H.
[b]CD$_3$OD.
[c]CDCl$_3$.

0.2 mL of 3N HCl was added to 200 mg of the crude Hippospongia sp. extract (in 20 mL methanol, and the mixture was refluxed for 2 hours. After cooling, the mixture was extracted with methylene chloride, then washed (3×) with DI water, dried with anhydrous sodium sulfate and purified on a flash column with 100% MeCl$_2$, then by RPHPLC using methanol-water gradient to give the alcohol Igernellin (6) as a colorless oil [α]$_D$=−30° (c 1.1 MeOH); $^1$H NMR and $^{13}$C NMR are shown in Table 1 above ESIMS m/z [M+H]$^+$=373.4. The alcohol (6) had properties generally identical to those described by Kernan et al., *Nat. Product Lett.* 1995, 7, 297–301 for Igernellin isolated from specimens of Igernella sp. from Palau.

Example 7

Extraction, Isolation and Identification of Halisulfate 7 (7) and the Corresponding Alcohol (8)

The extract of Hippospongia sp. (UCSC collection number 97220) described above in Example 6 also yielded (+) Halisulfate 7 (2) as a colorless oil, [α]$_D$=+17° (c 10.1 CHCl$_3$); HRFABMS m/z [M−Na]$^-$=451.2508 (calcd for C$_{25}$H$_{39}$O$_5$S, 451.2518). Hydrolysis of the crude sponge extract in the manner described in Example 6 yielded the alcohol (8) as a colorless oil [α]$_D$=+37° (c 4.5 MeOH). The $^1$H NMR, and $^{13}$C NMR for (7) and (8) were generally identical to those reported by Fu et al., *J. Nat. Prod.* 1999, 62, 1190–1191.

Fu et al. also reported the isolation of Halisulfate 5 (not shown) from Hippospongia sp. However, no Halisulfate 5 was found in the Hippospongia sp. samples used in this example. Halisulfate 5 is considered to be a halicondric terpenoid within the scope of the present disclosure.

Example 8
Extraction, Isolation and Identification of Hipposulfate D (9) and the Corresponding Alcohol (10)

Samples of Hippospongia sp. (order Dictyoceratida, family Spongiidae, UCSC collection number 90176) were obtained at approximately 15 meters depth off Papua New Guinea, and were extracted with MeOH. Step gradient column chromatography (methylene chloride/methanol) of the extract provided fractions which were further purified by RPHPLC to yield Hipposulfate D (9) as a brown waxy solid, $[\alpha]_D=+60°$ (c 0.27 MeOH); HRFABMS m/z [M+Na+Na−H]$^+$=591.2272 (calcd for $C_{31}H_{45}O_6SNa_2$, 591.2732). $^1$H NMR and $^{13}$C NMR are shown in Table 2

TABLE 2

NMR Data for Hipposulfate D (9) and Corresponding Alcohol (10).

| | hipposulfate D (9)[b] | | alcohol (10)[c] | |
|---|---|---|---|---|
| atom | $\delta_C$ (mult) | $\delta_H$ (mult, JHz) | $\delta_C$ (mult) | $\delta_H$ (mult, JHz) |
| 1 | 39.7 (t) | 1.73/ (m) 1.15 | 39.4 (t) | 1.80/ (m) 0.96 |
| 2 | 19.7 (t) | 1.43 (m) | 18.6 (t) | 1.42 (m) |
| 3 | 43.3 (t) | 1.35/ (m) 1.16 | 42.3 (t) | 1.37/ (m) 1.12 |
| 4 | 33.6 (s) | | 32.4 (s) | |
| 5 | 51.0 (d) | 1.24 (m) | 50.2 (d) | 1.27 (m) |
| 6 | 24.8 (t) | 1.88 (m) | 24.0 (t) | 1.96/ (m) 1.83 |
| 7 | 122.8 (d) | 5.29 (br m) | 122.3 (d) | 5.40 (br m) |
| 8 | 136.8 (s) | | 135.2 (s) | |
| 9 | 49.4 (d) | 2.23 (m) | 50.4 (d) | 1.96 (m) |
| 10 | 37.5 (s) | | 36.4 (s) | |
| 11 | 27.3 (t) | 1.60 (m) | 21.8 (t) | 1.48 (m) |
| 12 | 84.3 (d) | 4.47 (m) | 76.2 (d) | 3.51 (m) |
| 13 | 38.0 (d) | 2.98 (m) | 40.1 (d) | 1.52 (m) |
| 14 | 34.4 (t) | 1.31/ (m) 1.13 | 32.4 (t) | 1.46/ (m) 1.08 |
| 15 | 35.0 (t) | 1.25 (m) | 31.4 (t) | 1.27 (m) |
| 16 | 42.0 (t) | 1.60 (m) | 41.3 (t) | 1.63/ (m) 1.58 |
| 17 | 79.0 (s) | | 78.3 (s) | |
| 18 | 131.8 (d) | 5.58 (dd, 7, 10) | 131.2 (d) | 5.57 (d, 10) |
| 19 | 123.3 (d) | 6.22 (d, 10) | 122.6 (d) | 6.25 (d, 10) |
| 20 | 33.6 (q) | 0.78 (s) | 33.1 (q) | 0.84 (s) |
| 21 | 22.3 (q) | 0.86 (s) | 21.9 (q) | 0.85 (s) |
| 22 | 22.9 (q) | 1.67 (s) | 22.6 (q) | 1.59 (s) |
| 23 | 14.0 (q) | 0.70 (s) | 15.2 (q) | 0.88 (s) |
| 24 | 13.5 (q) | 0.91 (d) | 13.7 (q) | 0.71 (d) |
| 25 | 26.2 (q) | 1.25 (m) | 26.1 (q) | 1.33 (s) |
| 1' | 122.8 (s) | | 122.0 (s) | |
| 2' | 113.5 (d) | 6.37 (s) | 112.9 (s) | 6.47 (d, 3) |
| 3' | 152.0 (s) | | 149.3 (s) | |
| 4' | 116.2 (d) | 6.58 (s) | 115.5 (d) | 6.57 (dd, 3, 9) |
| 5' | 117.3 (d) | 6.58 (s) | 116.7 (d) | 6.61 (d, 9) |
| 6' | 147.7 (s) | | 147.1 (s) | |

[a]Spectra were recorded at 62.5 MHz for $^{13}$C and 250 MHz for $^1$H.
[b]CD$_3$OD.
[c]CDCl$_3$.

Hydrolysis of the crude sponge extract using the procedure of Example 6 yielded the alcohol (10) as a brown waxy solid: HRFABMS m/z [M+K]+=505.3045 (calcd. for C31H45O3K, 505.3084); 1H NMR and 13C NMR are shown in Table 2 above

Example 9
Extraction, Isolation and Identification of Dictyodendrillin B (11) and Dictyodendrillin C (12)

Specimens of the sponge *Cacospongia mycofijiensis* were collected off Fiji at approximately 15 meters depth. Sponge samples were extracted with 100% MeOH and purified on Biotage Si gel columns using methylene chloride and EtOAc/Hexane (50/50) to provide an oil containing both dictyodendrillin B (11) and dictyodendrillin C (12) and having generally the properties reported by Tran et al., *Aust. J. Chem.* 1995, 48, 1757–1760. RPHPLC of the oil subsequently yielded dictyodendrillin B (11) and dictyodendrillin C (12). HRFABMS reported a [M−CO$_2$H]$^+$=205.1581, Δ 1.1 mmu calc. and a [M−CO+H]$^+$=223.1789, A 3.5 mmu calc. for $C_{15}H_{22}O_3$.

Example 10
Extraction Isolation and Identification of Heteronemin (13)

Specimens of Heteronema sp. were collected approximately 15 meters depth off Papua New Guinea. Sponge samples were extracted with petroleum ether, and heteronemin (13), was crystallized directly from the crude extract and purified by recrystallization from pet. Ether to show a melting point of 176.5–177° C. $^1$H NMR was generally identical to that reported by Kazlauskas et al., *Tet. Lett.* 1975, 30, 2631–2634.

Example 11
Lipoxygenase Assay 15-human lipoxygenase (15-HLO) was expressed and purified as described by Holman et al., *J. Am. Chem. Soc. B* 1998, 120, 12564–12577. 15-HLO enzyme activity was determined by direct measurement of the product formation of a 3 μM linoleic acid solution by monitoring the increase of absorbance at 234 nm in 25 mM Hepes (pH 7.5), 0.2% (g/L) cholic acid. All reactions were performed in 2 ml of buffer (approx. 200 nM 15-HLO) under constant stirring at approximately 22° C. IC$_{50}$ values were determined by measuring the enzymatic rate at a variety of inhibitor concentrations (depending upon inhibitor potency) and plotting their corresponding values versus inhibitor concentration. The corresponding data was fit to a simple saturation curve and the inhibitor concentration at 50% activity was determined. The subject inhibitors used in the assay were dissolved in MeOH at a concentration of approximately 25 mg/ml.

Out of an initial set of 100 crude extracts evaluated in the 15-HLO assay, one of these exhibited potent lipoxygenase inhibition activity at a sub μg/mL level. The single potent extract of this set was from a Papua New Guinea sponge, Suberea sp. (Order: Verongida. Family: Aplysinellidae, coll. no. 97243) and its IC$_{50}$ of 0.1 μg/mL merited bioassay guided follow-up using the 15-HLO screen. Table 3 shows the 15-HLO inhibition activity of some of the crude sponge extracts.

TABLE 3

15-HLO Inhibition Activity of Crude Sponge Extracts.

| Sponges | Coll No. | Site | IC$_{50}$ (μg/mL) |
|---|---|---|---|
| Suberea sp. | 97243 | Papua New Guinea | 0.1 ± 0.02 |
| J. splendens | 94541 | Indonesia | 150 ± 15 |
| " | 95077 | Papua New Guinea | 45 ± 5 |
| " | 96117 | Papua New Guinea | 0.4 ± 0.02 |
| " | 96555 | Indonesia | 6.5 ± 3 |
| " | 97238 | Papua New Guinea | >300 |

Inspection of the NMR and MS data for the active crude extract of Suberea sp. coll. no. 97243 and semi-pure fractions indicated the presence of several compounds possessing aliphatic methyls appearing as intense $^1$H NMR singlet resonances. At varying stages of the isolation, especially as pure substances were obtained, these were first evaluated in the 15-HLO assay and then via standard structural-dereplication procedures. Two of the compounds proved to be known; jaspaquinol (3), IC$_{50}$=0.3 µM, and (−)-jaspic acid (4), IC$_{50}$=1.4 µM. The striking potency of these compounds as 15-HOL inhibitors has heretofore been unrecognized. This same pair of compounds was also isolated from *Jaspis splendens*, the well known source of (+)-jasplakinolide (not shown) by Murray et al., *J. Org. Chem.* 1997, 62, 5638–5641. The two new compounds isolated from Suberea sp. and disclosed herein are (−)-subersic acid (1), IC$_{50}$=15 µM, and (+)-subersin (2), IC$_{50}$ >100 µM. The activity in the extracts from *J. splendens* samples is believed to be due to the presence of jaspaquinol (3) and (−)-jaspic acid (4) therein.

Table 4 shows the 15-HLO inhibition activity of these compounds together with the standards NDGA (De Vries et al., *Biochem Pharmacol.* 1988, 37, 2899–2905) and oleyl sulfate (Mogul et al., *Biochem.* 2000, 39, 4801–4807).

TABLE 4

15-HLO Inhibition Activity of Compounds (1)–(4)

| Compound | IC$_{50}$ (µM) |
| --- | --- |
| (−)-subersic acid (1) | 15 µM |
| (+)-subersin (2) | >100 µM |
| jaspaquinol (3) | 0.3 µM |
| (−)-jaspic acid (4) | 1.4 µM |
| NDGA | 0.3 µM |
| oleyl sulfate | 0.4 µM |

Hipposulfate C (5) and the corresponding alcohol igernellin (6), halisulfate 7 (7) and the corresponding alcohol (8), hipposulfate D (9) and the corresponding alcohol (10), dictyodendrillin B and C (11), (12), and heteronemin (13), while not tested with the assay, are believed to be potential lipoxygenase inhibitors due to their structures and biological sources.

The 15-HLO inhibition assay as used herein is both a robust tool and a reliable reporter of lipoxygenase inhibition which avoids inconsistent behavior reported for the 5-HLO assay by Cabre et al., supra.

There are multiple pathways currently known to inactivate lipoxygenases ranging from competitive, allosteric, to reductive inhibition. Having a series of LO inhibitors in hand as provided by the subject compounds of the invention provides an opportunity to explore the requirements of such alternative pathways. On the one hand, NDGA is known to be a LO redox inhibitor that reduces the active Fe(III) enzyme to the inactive Fe(II) enzyme (Kemal et al., *Biochem.* 1987, 26, 20764–7072). This mode of action appears to be responsible for the inhibition by jaspaquinol (3) (IC$_{50}$=0.3), because of the reduction of the active site ferric ion as seen by fluorescence spectroscopy. (Agro et al., *FEBS Lett.* 1975, 52, 73–76). It is contemplated that the hydroquinol residue of (3) reduces the iron. A similar mechanism may be operating for sponge derived polybrominated phenols and diphenyl ethers that are known 15-HLO inhibitors ((Fu et al., *J. Nat. Prod.* 1995, 58, 609), which show IC$_{50}$ from 1–7 µM.

It is also contemplated that (−)-subersic acid (1) and (−)-jaspic acid (4) operate by a non-redox inactivation mechanism with 15-HLO. This conclusion is based on the observation that these compounds do not cause a change in the fluorescence spectroscopy of 15-HLO (i.e. no reduction of Fe(III)). While (−)-jaspic acid (4) and (−)-subersic acid (1) are potent inhibitors of 15-HLO with IC$_{50}$=1.4 and 15 µM, respectively, they exhibit differential activity of approximately 10-fold. While extensive SAR conclusions have not been drawn at this point, it is noteworthy is that the polar head groups are the same for (1) and (4), indicating their polyunsaturated spacers are critical for inhibition. The structural parallelism between (4) and arachidonic acid may be of significance. Both have a similar spatial separation between the unsaturated functionality that undergoes dioxygen incorporation by 15-HLO and the carboxylic head group. In arachidonic acid this involves the 14, 15 double bond while in the case of (4) the side-chain, tri-substituted double bond is bound in a similar location, but it can not undergo oxygenation possibly due to the lack of a 1,4 diene functionality.

Example 12

Isolation and Culture of Primary Hippocampal Neuronal Cells

Neurobasal medium (Life Technologies, Rockville, Md.) with 1× B27 supplement (Life Technologies), 0.5 µM L-glutamine, 25 µM L-glutaxnic acid, and 1× Penicillin/Streptomycin was prepared fresh prior to use. Hank's Basic Salt Solution (HBSS, Ca/Mg-free) was prepared by preparing 1× Hanks CMF (Gibco) supplemented with HEPES (10 mM, pH 7.3), sodium bicarbonate (0.35%), 1× Penicillin/Streptomycin, and 1 mM pyruvate. Poly-D-lysine (Sigma, St. Louis, Mo.) was prepared by filtering a 50 µg/ml solution through 0.2 µm filter tubes. Sigmacote (Sigma, St. Louis, Mo.). Plastic Culture Flasks (T75 cm$^2$) or 12-well cell culture plates were then treated with Poly-D-Lysine (Sigma, St. Louis, Mo.).

Pregnant female mice (E18–E19) were euthanized with $CO_2$ prior to removal of the uterus, which was then placed in a sterile plastic petri dish. The embryos were removed from the sac, and the embryonic brains removed and immersed in cold (4° C.) Hepes Buffered Salt Solution (HBSS; Ca/Mg free; Life Technologies) in a small petri dish. Hippocampi were then removed from the brains under a dissecting microscope and were placed on a paraffin-covered dish. The meninges were stripped away and the dissected hippocampi were collected in a small petri dish in HBSS. The hippocampi were transferred to a 15-ml centrifuge tube (normally 10–12 brains per tube) filled with HBSS. The tube containing the brains was centrifuged at 1000 rpm for 2 minutes in a GH 3.8 A rotor in an Allegra Centrifuge (Beckman Instruments, Fullerton, Calif.). The supernatant was removed, 2 ml of HBSS was added to the hippocampi in the tube, and the resulting suspension was triturated 2 times each with long-tipped siliconized glass pipettes having progressively smaller apertures, starting with a pipette with a standard size opening (approximately 1.0 mm diameter), following with one having an aperture of half standard size (approximately 0.5 mm diameter), then with one having an aperture about one-half that size (0.25 mm diameter). The suspension was then centrifuged again at 1000 rpm for 2 min in a tabletop centrifuge, the supernatant was discarded, and 2 ml of Neurobasal/B27i (with antibiotics) was added to the tube. The trituration procedure described above was then repeated on this suspension.

The density of cells was determined on a small aliquot of cells using standard counting procedures and correcting for cell viability by trypan blue stain exclusion. Using this procedure, the expected yield is $3 \times 10^5$–$6 \times 10^5$ cells/brain. Cells were then added to PDL-coated 12 well plates, flasks or MetTek dishes in Neurobasal/B27I at a density of about $1.5 \times 10^6$ cells (T75 flask) or about 100,000 cells/well of a 12-well plate. Plated cells were incubated at 37° C. with 5% $CO_2$ in air atmosphere. Media was renewed after 3–4 days by replacing half of it with fresh Neurobasal/B27m medium, containing 5 µM cytosine arabinoside (AraC). Seven to eight days from the initial culture, the media was renewed again, by removing one-half or it and replacing with an equal amount of fresh Neurobasal/B27m medium (without Ara-C).

Example 13

Hippocampal Anoxia-Reoxygenation Cell Death Assay

This assay was used to induce ischemia by anoxia-reoxygenation in cultured hippocampal neuronal cells. Test compounds were added to assess potency and efficacy against ischemia-induced neuronal cell injury and cell death.

Neurobasal media, NoG neurobasal media, B27 supplement and B27 Supplement minus AO were obtained from Life Technologies. Neurobasal/B27 medium was prepared with 2× B27 minus AO supplement, 0.5 mM L-glutamine and 0.25× penicillin/streptomycin. Cell Tracker Green was obtained from Molecular Probes and a fresh 5 μM solution was prepared from 10 mM stock just before use. NoG-Neurobasal contains NoG neurobasal medium plus 0.5 mM glucose, 0.1 mM L-glutamine and 0.25× Penicillin/Streptomycin. Primary hippocampal neuronal cells were prepared according to the methods described above and were cultured in poly-D-lysine coated 12 well plates for 10-11 days prior to use.

Deoxygenated LoG-Neurobasal medium (100 ml) was prepared by pre-equilibrating the medium in a T150 cm$^2$ flask in a hypoxic chamber overnight (0.5% $O_2$, 85% $N_2$, 5% $CO_2$ & 10% $H_2$). Following pre-incubation under hypoxic conditions, the LoG-Neurobasal media was lightly bubbled with 100% $N_2$ for 30 min to completely deoxygenate the media. An additional 20 ml of LoG-Neurobasal was pre-equilibrated in a T75 cm$^2$ flask and 100 ml Neurobasal/B27AO was incubated in a normal incubator (5% $CO_2$ in air atmosphere) overnight. Reoxygenated medium was prepared by placing medium overnight in the culture incubator prior to use.

Existing culture medium (Neurobasal/B27m) was removed from the cells by aspiration. Cells were washed once with 2 ml/well (12-well culture plates) of glucose free-BSS. Neurons were replenished 10-11 days after initial culture with deoxygenated LoG-Neurobasal (1 ml per well for each well of a 12-well plate). Compounds (1), (2) and (5)-(13) were individually added directly to each well (usually 3 concentrations of the compound plus positive control, each in triplicate), wherein the compounds contacted cells. The compounds were dissolved in 100% DMSO prior to addition to the wells, with the concentrations adjusted such that the final concentration of DMSO in the cell media never exceeded 0.5%.

To induce ischemia by hypoxia-reoxygenation, plates containing cells with test compounds were placed in a hypoxic chamber for 5 hr with the plate lids ajar. For normoxia controls, pre-equilibrated normoxic LoG-Neurobasal medium was added to each well of cells, and the plate was replaced in the normal culture incubator for 5 hr. After 5 hr of hypoxia, the existing media was carefully aspirated off, and 2 mL of new, reoxygenated (pre-equilibrated) Neurobasal/B27AO was added to each well. The same test compounds (1)-(5), (7)-(9), (11) and (13) (in the same the concentrations) were added back into the corresponding wells. Plates were placed in the cell culture incubator (5% $CO_2$/air atmosphere) and reoxygenated for 20-24 hr. After reoxygenation for 20-24 hr, live neurons were quantitated using the cell tracker green fluorescence method.

To test for cell viability, existing culture medium was aspirated from each well of the 12 well plates, and neurons were washed once with 2 ml of HBSS (pH 7.4, prewarmed to 30-37° C.). To each well was added 1 ml of 5 μM Cell Tracker Green fluorescent dye dissolved in HBSS. Plates were placed in the dark at room temperature for 15 minutes, then were washed with 2 ml of HBSS. One milliliter of HBSS was then added to each well, and fluorescent cells were counted using a fluorescent microscope. A significantly increased cell viability compared to hypoxia-reoxygenated cells is indicative of the efficacy of a compound. The results of this assay for compounds (1)-(5), (7)-(9), (11) and (13) are shown in Table 5.

TABLE 5

Hippocampal Anoxia Assay

| Compound Tested | Percent Activity (Dose for Max. Activity) |
|---|---|
| (−)-Subersic acid (1) | No activity at 10 μg/mL |
| (+)-Subersin (2) | 1 μg/mL (30%) |
| Jaspaquinol (3) | 0.1 μg/mL (20%) |
| (−)-Jaspic acid (4) | 1 μg/mL (63%) |
| Hipposulfate C (5) | 10 μg/mL % |
| Halisulfate 7 (7) | No activity at 10 μg/mL |
| Halisulfate 7 alcohol (8) | No activity at 10 μg/mL |
| Hipposulfate D (9) | No activity at 10 μg/mL |
| Dictyodendrillin B (11) | 0.1 μg/mL (56%) |
| Heteronemin (13) | 0.1 μg/mL (21%) |

As can be seen from Table 5, (+)-Subersin (2), Jaspaquinol (3), (−)-Jaspic acid (4), Hipposulfate C (5), Dictyodendrillin B (11) and Heteronemin (13) increased cell viability. While dictyodendrillin C was not tested (because of insufficient quantity available), it is believed that dictyodendrillin C would show relatively high activity due to its similar structure: to its high activity isomer dictyodendrillin B.

Example 14

Isolation and Culture of Primary Neonatal Cardiomyocytes

10× Heart Dissection Solution (HDS) contains the following components (g/l) in tissue culture grade water: NaCl, 68; HEPES, 47.6; $NaH_2PO_4$, 2; Glucose, 10; KCl, 4; $MgSO_4$, 1, pH adjusted to 7.4. Prior to filter sterilization of diluted (1× HDS) solution, 10 mg phenol red was added to each 500 milliliters of medium. Transferrin and Bovine Insulin were obtained from Life Technologies, and resuspended at a concentration of 4 mg/ml in tissue culture grade water. DMEM-F12- DMEM/F12, powder, 1:1 containing glutamine and pyridoxine hydrochloride was purchased from Life Technologies. To one liter equivalent of the powder was added 2.43 g of sodium bicarbonate and 10 ml of 100× Penicillin/Streptomycin in 950 ml of tissue culture grade water with stirring. The pH was adjusted to 7.2 with 1M HCl and volume was adjusted to 1 liter. The solution was filter sterilized then 2.5 ml of 4 mg/ml Transferrin, 250 μl 4 mg/ml Insulin and 30.7 mg of bromodeoxyuridine were added. DMEM-F12 was also prepared with 4% FBS for pre-coating the tissue culture plates and initial suspension of the cardiomyocyte pellet. Collagenase solution-49 mg of collagenase was resuspended in 120 ml 1× HDS.

Tissue culture plasticware was pre-coated with DMEM-F12-4% FBS by incubating 50 μl per well of a 96-well plate. Two-day old rat pups were removed from their mothers and placed in a sterile container. Pups were dipped quickly into 70% alcohol, then decapitated and the body was placed in an empty sterile tissue culture dish. An incision was made starting at the neck and progressing towards the belly, cutting through the sternum. The heart was removed and placed in a tissue culture dishes containing 1× HDS. The atria were trimmed, and the remaining ventricles were placed into a separate tissue culture dish containing 1× HDS, where they were sectioned into 3-4 pieces each. Ventricles were then transferred to a sterile 250 ml glass flask and the 1× HDS was removed. Twenty milliliters of pre-warmed collagenase solution were added to the ventricles, followed by incubation at 37° C. with shaking. After 30 minutes, the collagenase solution was removed and replaced with 20 ml fresh pre-warmed collagenase. Incubation was continued for an additional 20 minutes. At the end of the incubation, any tissue chunks were allowed to settle prior to removing the collagenase (containing the isolated cardiomyocytes) from the disrupted tissue pieces. The isolated myocytes were added to a 50 ml Falcon tube containing 2 ml Fetal Bovine Serum (FBS). The remaining tissue pieces were subjected to a second digestion by adding 20 ml fresh pre-warmed collagenase and incubating as above for 20 minutes. This second digest was then centrifuged at 1000 rpm for 10 minutes in a GH 3.8 A rotor in an Allegra 6 Centrifuge (Beckman Instruments, Fullerton, Calif.). The resulting supernatant was discarded, and the cell pellet was suspended with 4 ml FBS. The resulting cell suspension was placed in the incubator at 37° C. This step was repeated several additional times to harvest additional material.

Percoll gradients were prepared by adding 2.5 ml of 10× HDS to 22.5 ml of Percoll (Life Technologies) with mixing (Percoll Stock). Top Gradient solution (11 ml Percoll Stock and 14 ml 1× HDS) and Bottom Gradient solution (13 ml Percoll Stock and 7 ml 1× HDS) were prepared. Four milliliters of the Top Gradient solution were transferred into 6×15 ml sterile Falcon tubes. Three milliliters of the Bottom Gradient solution were placed in each tube by inserting a serological pipette to the bottom of the tube and slowly adding the liquid.

All the digests (5 in total) were pooled in one 50 ml Falcon tube and centrifuged on a tabletop Allegra 6 Centrifuge (Beckman Instruments, Fullerton, Calif.) using a GH 3.8 A rotor at 1000 rpm for 10 minutes. The supernatant was discarded, and the cell pellet was resuspended in 12 ml of 1× HDS. Two milliliters of the cell suspension was added to the top of each gradient. The gradient tubes were then centrifuged at 3000 rpm for 30 minutes without braking in a GH 3.8 A rotor in an Allegra 6 Centrifuge (Beckman Instruments, Fullerton, Calif.). Following centrifugation, the cells segregated into two sharp bands at the two interfaces. The lower band of the two bands was enriched for cardiomyocytes; there was also a cardiomyocyte pellet at the bottom of the tube. The upper band was enriched for fibroblasts and other non-cardiomyocytes. The upper portion of the gradient was aspirated down to just above the cardiomyocyte layer. The cardiomyocyte layer was then carefully removed along with the pellet, and the two fractions were pooled in a sterile 50 ml Falcon tube, along with corresponding fractions from additional gradient tube; then 1× HDS was added to a total volume of about 50 ml. The tube was centrifuged at 1000 rpm for 7 minutes. The supernatant was discarded and resuspended in 25 ml 1× HDS. A further 25 ml of 1× HDS was added and the centrifugation step was repeated. The cell pellet was resuspended carefully but thoroughly in 40–50 of DMEMF12-4% FBS.

A small aliquot of the cell suspension was counted in a hemocytometer. The DMEM/F12-FBS coating medium was aspirated from the tissue culture dishes. The cardiomyocytes were added to the dishes at a plating density of $7.5 \times 10^4$/well per 96-well in 200 µL and $1.5 \times 10^5$/well per 12-well in 3 ml. The cultures were incubated at 37° C. with 5% $CO_2$ overnight. The original medium was removed, and fresh DMEM/F12-5% FBS added to each culture, prior to incubation at 37° C. with 5% $CO_2$ in air atmosphere for a further 48 hours, before use.

Example 15

Myocyte Calcium-Contractility Assay

Complete DMEM-F12: DMEM/F12, powder, 1:1 containing glutamine and pyridoxine hydrochloride was purchased from Life Technologies (Invitrogen Life Technologies, Carlsbad, Calif.). Powder sufficient to prepare one liter of buffer and 2.43 g of sodium bicarbonate was mixed into 950 ml of tissue culture grade water. The pH was adjusted to 7.2 with 1M HCl and the remaining water was added to make 1 liter. Following filter sterilization, 10 ml of 100× Penicillin/Streptomycin, 2.5 ml of 4 mg/ml Transferrin, 250 µl 4 mg/ml Insulin and 30.7 mg of bromodeoxyuridine were added, and the mixture was incubated at 37° C. prior to use. 1 mM glucose in DMEM was made from DMEM without L-glutamine, without glucose, without sodium pyruvate, purchased from Life Technologies. 20 µM Fluo-4: Cell permanent AM ester of Fluo-4 was obtained from Molecular Probes (Eugene, Oreg.) as a dry powder to be stored at −20° C. This fluorescent dye is light sensitive and was made up fresh at 1 mM in DMSO prior to use to prevent light degradation. 10 mM $CaCl_2$ solution was made fresh each day in 1× HBSS and incubated at 37° C. prior to use.

Neonatal cardiomyocytes were isolated as described above. The cardiomyocytes were plated in 96-well format (black clear-bottomed plates) at a density of $7.5 \times 10^4$ per well and grown for 2 days in the presence of 5% FBS prior to use in the assay.

Physiological ischemia was simulated by placing the cardiomyocytes in an anaerobic chamber (0% $O_2$, 85% $N_2$, 5% $CO_2$ & 10% $H_2$) in DMEM containing 1 mM glucose for 16 hr. The cardiomyocytes were then reoxygenated with DMEM-F12 for 2 hr. Positive control cells are treated with DMEM-F12 containing 25 mM Glucose, which protects against the anoxia.

The compounds tested, (1)–(5), (7)–(9), and (11)–(13), were made up in DMEM-1 mM glucose in 96 deep-well mother plates and appropriately diluted for use in the assay. The media was removed from the cells and replaced with 200 µl of either DMEM-F12 or 1 mM Glu DMEM with or without the test compounds. The plates were then placed inside the 37° C. incubator in the anaerobic chamber and incubated for 16 hours. The plates were then removed and reoxygenated by the addition of DMEM-F12. The DMEM with or without the subject compounds was carefully removed from the cells and replaced with pre-warmed DMEM-F12 containing 5% FBS. Since the anoxic treatment may damage and/or kill the cells, causing them to dislodge from the bottom of the wells gentle aspiration of media is required at this step. The cells were then placed in a normal incubator at 37° C. and incubated for two hours to allow the cells to reoxygenate.

A working solution of 20 µM Fluo-4 was added to pre-warmed 1× HBSS. The cells were loaded with Fluo-4 by first removing media from the cells and replacing with 100 µl of 20 µM Fluo-4. Unloaded control cells were treated in parallel with 1× HBSS alone. All cells were then incubated at 37° C. for 30 minutes. Before fluorescence measurements were made, the cells were washed in indicator-free medium (HBSS) to remove any dye that is non-specifically associated with the cell surface. Cells were then incubated for an additional 20 minutes at room temperature. Basal Fluo-4 fluorescence was measured using the 485 nm excitation and 538 nm emission filter pair on a microplate flourometer (Fluorskan™, Thermo Labsystems Oy, Helsinki, Finland). Each well was read for 160 ms to obtain a baseline reading, then stimulated to contract by addition of 10 mM $CaCl_2$.

Following incubation at 37° C. for 30 minutes, a stimulated fluorescence reading was taken after 90 minutes. The activities for the several compounds tested, as determined via measured fluorescence, are shown in Table 6.

TABLE 6

Cardiomyocite Beating Anoxia Assay

| Compound Tested | Percent Activity (Dose for Max. Activity) |
| --- | --- |
| (−)-Subersic acid (1) | 25 μg/mL (61%) |
| (+)-Subersin (2) | 8 μg/mL (78%) |
| Jaspaquinol (3) | No activity at 75 μg/mL |
| (−)-Jaspic acid (4) | 3 μg/mL (59%) |
| Hipposulfate C (5) | No activity at 75 μg/mL |
| Halisulfate 7 (7) | 25 μg/mL (77%) |
| Halisulfate 7 alcohol (8) | No activity at 75 μg/mL |
| Hipposulfate D (9) | 75 μg/mL (70%) |
| Dictyodendrillin B (11) | No activity at 100 μg/mL |
| Dictyodendrillin C (12) | 100 μg/mL (46%) |
| Heteronemin (13) | No activity at 100 μg/mL |

As can be seen from Table 6, (−)-Subersic acid (1), (+)-Subersin (2) (−)-Jaspic acid (4), Halisulfate 7 (7), Hipposulfate D (9) and Dictyodendrillin C (12) resulted in increased cell viability.

Example 16
Rat Middle Cerebral Artery Occlusion (MCAO) Model of Cerebral Ischemia
A. Animal Preparation Male Wistar rats (Harlan, Ind.) weighing 300–350 g are commonly used in these experiments. Animals are allowed free access to water and commercial rodent diet under standard laboratory conditions. Room temperature is maintained at 20–23° C. and room illumination is on a 12/12-hour light/dark cycle. Animals are acclimatized to the laboratory environment 5 to 7 days prior to the study, and fasted (with free access to water) overnight before surgery.
B. Middle Cerebral Artery Occlusion (MCAO)

Anesthesia is maintained by inhalation of 3.0% isoflurane (Aerrane, Front Dodge, Iowa) in 0.8% oxygen. The animal's neck is shaved and sterilized before operation. Body temperatures are controlled and maintained at 37.5° C+/−1 degree via external heating and cooling devices. To lower the body temperature, animals are placed in a cooling chamber that uses ice to cool circulating air. Throughout the study the body temperature is recorded using a temperature transponder (BMDS Inc., Seaford, Del.) implanted subcutaneously at the time of MCAO between the rat shoulder blades, which allows the user to read the body temperature via a pocket scanner (BMDS Inc., Seaford, Del.). The body temperature can also be taken by inserting the temperature probe into the animal's rectum. Body temperature is recorded every hour for 6 hours post-occlusion, but temperature is measured more frequently to facilitate maintaining the animals' normothermic temperature.

Animals are subjected to two hours MCAO using a modified intraluminal filament technique, as follows. A midline incision on the ventral part of the neck is made to expose external and internal carotid arteries. The right external and common carotid arteries are ligated by a suture (silk 5/0, Carlisle Laboratories, Farmers Branch, Tex.) and the right internal artery is temporarily ligated using a microvascular clip (Fine Science Tool Inc., Foster City, Calif.). A small incision is made in the common carotid artery. A nylon filament, its tip rounded by heating, is prepared from a fishing line (Stren Fishing Lines, Wilmington, Del.) and is inserted from the right common carotid artery. The filament is advanced into the internal carotid artery 18–20 mm from the point of bifurcation of internal and external arteries and a suture is tightly ligated around the filament. Two hours post occlusion, animals are re-anesthetized to allow reperfusion for the remaining of the experiment by removal of the filament.
C. Drug Administration Test compounds can be administered by any of a number of routes, such as those described below. Compounds can be administered before, during or after occlusion, as appropriate to the protocol.

a) Intracerebroventricular (ICV) Infusion

The anesthetized animal is placed on a stereotaxic apparatus (Harvard Apparatus, S. Natick, Mass.). Anesthesia is maintained by inhalation of 3.0% isoflurane (Aerrane, Front Dodge, Iowa) in 0.8% oxygen throughout the entire procedure. The scalp is shaved and sterilized prior to surgery. A midline sagittal incision about 3 cm long is made slightly behind the eyes to expose the skull. The skull is scraped with a rounded end spatula to remove periosteal connective tissue. A bur hole is placed 1.5 mm lateral, 1 mm posterior to the left of the bregma to mark the left lateral ventricle. A brain infusion cannula (ALZET—Alza, Palo Alto, Calif.) is inserted 4 mm deep into the hole. The desired depth is adjusted by attaching spacers to the cannula. The cannula, attached to a 4-cm silastic catheter (Helix Medical Inc., Carpinteria, Calif.), is fixed in place with dental cement (Ketac-cement, Norristown, Pa.). The catheter is either attached to a primed osmotic pump placed subcutaneously between the shoulder blades for permanent infusion or to a syringe for a short infusion.

b) Intravenous (IV) Osmotic Pump Implantation Into the Jugular Vein

Anesthesia is maintained by inhalation of 3.0% isoflurane (Aerrane, Front Dodge, Iowa) in 0.8% oxygen throughout the entire procedure. The animal's neck is shaved and sterilized before operation. A midline incision is made on the ventral part of the neck to exposes the jugular vein. The vein is isolated and ligated with a suture (silk 510, Carlisle Laboratories, Farmers Branch, Tex.) rostral to the point of the incision and a microvascular clip (Fine Science Tool Inc., Foster City, Calif.) is placed close to the heart. A small incision is made between the two ligations. A 2-cm silastic catheter (Helix Medical Inc.) attached to a PE-60 tube (Becton. Dickinson and Co. Sparks, Md.) connected to an ALZET (Alza, Palo Alto, Calif.) pump is introduced and advanced 2 mm into the jugular vein toward the heart. The microvascular clip is removed and the catheter is secured in place with a suture (silk 5/0, Carlisle Laboratories, Farmers Branch, Tex.). The pump is placed into a pocket made subcutaneously between the shoulder blades, allowing the catheter to reach over neck to the jugular vein with sufficient slack to permit free movement of neck and head.

c) IV Infusion via Femoral Vein

Anesthesia is maintained by inhalation of 3.0% isoflurane (Aerrane, Front Dodge, Iowa) in 0.8% oxygen throughout the entire procedure. The exterior site of the right femoral vein is shaved and sterilized prior to surgery. A 3-cm incision is made in the right groin region and the femoral vein is isolated. A small incision is made on the femoral vein, temporarily ligated with a microvascular clip, to introduce and advance a polyethylene (PE-50) catheter (Becton Dickinson and Co. Sparks, Md.). The catheter is secured in place with suture (silk 5/0, Carlisle Laboratories, Farmers Branch, Tex.). The other end of the catheter is attached to a syringe filled with the heparinized saline for the bolus injection. Using a hemostat, a pocket is made subcutaneously on the back of the animal so the PE catheter can be brought up to the exteriorization point at the nape of the neck for either a bolus injection or a continuous injection by an osmotic pump.

d) Intraperitoneal (IP) Injection

An awake rat is held in a standard hand hold position, a 23¾G needle is injected into the lower right quarter of the abdomen past the peritoneum, slightly off the midline. To avoid organ injection, the plunger of the syringe is slightly pulled back. If no fluid is withdrawn, the content of the syringe is delivered into the abdominal cavity.

e) Gavage Feeding

A standard rat gavage tube (Popper & Sons Inc., NY) is attached to a 3-cc hypodermic syringe. The animal is held by the shoulder in a vertical position. The feeding tube is placed into the mouth then advanced until it reaches the stomach (the approximate insertion length of the tube was measured prior to the feeding). The content of the syringe is slowly delivered, and then the tube is withdrawn.

D. Behavioral Assessment

One hour after MCAO, the animal is gently held by its tail and observed for forelimb flexion. Then the animal is placed on the floor to be observed for walking pattern; only the animals that score 3 on the Bederson grading system (Table 7) are included in the study.

TABLE 7

Bederson Grading System for Neurological Evaluation

| Neurological deficit | Grading | Behavioral observation |
|---|---|---|
| Normal | grade 0: | No observable deficit |
| Moderate | grade 1: | forelimb flexion |
| Severe | grade 2: | forelimb flexion, decreased resistance to lateral push |
|  | grade 3: | forelimb flexion, decreased resistance to lateral push, circle to paretic side |

E. Evaluation of Ischemic Damage

Twenty-four hours post-MCAO, or longer in some experiments, animals are sacrificed by $CO_2$ asphyxiation (dry ice). The brain is quickly removed from the skull, using standard procedures, rinsed in chilled saline solution, and placed on a rat brain tissue slicer (ASI instrument, MI). Seven 2-mm thick coronal slices are cut from each brain using razor blades. The slices are immersed in 0.9% saline containing 1.0% 2,3,5-triphenyltetrazolume chloride (TTC) (Sigma Chemical Co., St. Louis, Mo.) and incubated in a 37° C. water bath for 30 minutes.

After staining, each 2-mm slice is photographed with a TMC-7 camera (JH Technologies, Ca) which is directly connected to a desktop PC to capture and save the image of each brain slice. This image is used for the measurements of the regions of interest using a computer-based image processing system (Metamorph).

To measure each area, the region of interest is selected using a freehand selection tool, the area is automatically computed by selecting the measure command. The measurements for primary regions of interest are right hemisphere, left hemisphere, total infarct, subcortical infarct, total penumbra and subcortical penumbra. After all regions of interest are measured for all seven slices of the brain, they are sorted by slice number and the corresponding regions of interest using an Excell macro called statistic final. This macro also calculates the cortical penumbra, cortical infarct and total ischemic damage for each slice; the corresponding areas of each rat brain are added together to produce a single measurement for each area. Since the ipsilateral hemisphere is swollen following MCAO, edema volume is calculated and reported as the volumetric differences between the right and left hemispheres of each brain slice. Using the % of hemispheric swelling all the volumes are corrected for the edema.

The volume of the damage is determined using the calculations below in Table 8 for each rat's brain.

TABLE 8

| Measurement | Equation | Corrected Value(s) |
|---|---|---|
| Cortical Penumbra (C.P.) | Total Penumbra − Subcortical Penumbra | Total Penumbra $(T.P._{corr}) =$ (T.P. × % H.S./100) $C.P._{corr.} = C.P. −$ (C.P. × % H.S./100) $S.P._{corr} = S.P. −$ (S.P. × % H.S./100) |
| Cortical Infarct | Total Infarct − Subcortical Infarct | $T.I._{corr.} = T.I. −$ (T.I. × % H.S./100) $S.I._{corr.} = S.I. −$ (S.I. × % H.S./100) $C.I._{corr.} = C.I. −$ (C.I. × % H.S./100) |
| Total Ischemic Damage (T.I.D.) | Total Penumbra + Total Infarct | $T.I.D._{corrected} =$ T.I.D. − (T.I.D. × % H.S./100) |
| Total Volume ($mm^3$) | Each value is multiplied by 2 (the thickness of the tissue). |  |
| Edema Volume | The volumetric differences between the sum of right and left hemispheres determines the edema volume. |  |
| % Hemispheric swelling (H.S.) | Edema × 100/left hemisphere |  |

F. Statistical Analysis

Sample size is chosen to achieve a 90% probability of significant results. The measurements representing the same region of interest in seven slices of each rat's brain are added together to yield a single measurement for total infarct, subcortical infarct, cortical infarct, total penumbra, subcortical penumbra, cortical penumbra, total ischemic damage and edema in each animal. Group data are presented as means +/−SEM. Differences at the level of $p<0.05$ are considered statistically significant. Between groups, comparisons of each region of interest are carried out by unpaired student t test (between two groups) or one way ANOVA followed by post hoc Bonferroni's multiple comparisons or by the nonparametric Dunnett's test (between control and the drug treated groups).

When tested as described above, compounds of the present invention provided a reduction in edema volume.

Example 17

Evaluations Of Sensorimotor Behavior

A. Fore and Hindlimb Grip Strength Test in Rats

Animals with cerebral infarction induced by transient or permanent unilateral occlusion of the middle cerebral artery (MCA) and sham-operated rats are tested for grip strength, a standard model of neuromuscular function and sensorimotor integration, using a Computerized Grip Strength Meter for Rats (Dual Stand Model, Columbus Instruments, Columbus, Ohio).

Animals are moved into the testing room for 30 minutes before testing. Prior to testing, each gauge is calibrated with a set of known weights and the apparatus is adjusted for the size of animal, according to manufacturer's instructions. The forelimb measurements are carried out with the meter in the tension peak mode to freeze the reading as the subject is pulled away from the grip bar. The hindlimb measurements are carried out with the meter in the compression peak mode to freeze the reading as the subject's hindlimbs are pulled over the bar toward the meter. Each animal is hand-held by the investigator as pulled past the grip bars, using a consistent technique, leaving the fore and hind limbs free to grasp the grip bars.

Testing is carried out on postoperative day 2 and repeated, in a blind-randomized fashion, twice weekly for a defined interval. Typically, three successive readings are taken for each animal with an intertrial interval long enough to record the data and zero both meters for the next trail.

B. Rota-Rod Test in Rats

Apparatus: Rota-Rod Treadmill for Rats (7750 Accelerating Model, from UGO BASILE, COMERIO-ITALY).

Procedure: Animals with cerebral infarction induced by transient or permanent unilateral occlusion of the middle cerebral artery (MCA) and sham-operated rats are tested in this study, using a Rota-Rod Treadmill for Rats (7750 Accelerating Model, UGO Basile, Comerio, Italy). The animals are moved into the testing room 30 minutes before testing. Every rat receives 2–3 training runs of 1–2 minutes at intervals of 2–3 hours before testing.

The cylinder on the apparatus is set in motion before placing the rats in position. The motor is set at a constant selected speed in 7700 on RESET mode, and the rats are placed, one by one, in their sections.

Testing is carried out on postoperative day 2 and repeated, in a blind-randomized fashion, twice weekly for a defined interval. Typically, three successive readings are taken for each animal with an intertrial interval long enough to record the data and zero both meters for the next trail.

The compounds of the present invention show activity when tested by this method.

Example 18

Model of Congestive Heart Failure

Experimental Preparation

225–275 g male Sprague-Dawley CD (Charles River) rats are used for this experiment. Animals are allowed free access to water and commercial rodent diet under standard laboratory conditions. Room temperature is maintained at 20–23° C. and room illumination is on a 12/12-hour light/dark cycle. Animals are acclimatized to the laboratory environment 5 to 7 days prior to the study. The animals are fasted overnight prior to surgery.

Animals are anaesthetized with ketamine/xylazine (95 mg/kg and 5 mg/kg) and intubated with a 14–16-gauge modified intravenous catheter. Anesthesia level is checked by toe pinch. Core body temperature is maintained at 37° C. by using a heating blanket. The surgical area is clipped and scrubbed. The animal is placed in right lateral recumbency and initially placed on a ventilator with a peak inspiratory pressure of 10–15 cm $H_2O$ and respiratory rate 60–110 breaths/min. 100% $O_2$ is delivered to the animals by the ventilator. ECG electrodes are placed to record a standard Lead II ECG. The surgical site is scrubbed with surgical scrub and alcohol. An incision is made over rib cage over the $4^{th}$–$5^{th}$ intercostal space. The underlying muscles are dissected with care to avoid the lateral thoracic vein, to expose the intercostal muscles. The chest cavity is entered through $4^{th}$–$5^{th}$ intercostal space, and the incision expanded to allow visualization of the heart. The pericardium is opened to expose the heart. A 6-0 silk suture with a taper needle is passed around the left coronary artery near its origin, which lies in contact with the left margin of the pulmonary cone, at about 1 mm from the insertion of the left auricular appendage. The coronary artery is occluded by tying the suture around the artery. The ECG is monitored for S-T changes indicative of ischemia. If the animal develops ventricular fibrillation, gentle cardiac massage is used to convert the animal to a normal rhythm. The incision is closed in three layers. The rat is ventilated until are able to ventilate on their own. The rats are extubated and recovered on a heating pad. Animals receive buprenorphine (0.01–0.05 mg/kg SQ) for post operative analgesia. Once awake, they are returned to their cage. Animals are monitored daily for signs of infection or distress. Infected or moribund animals are euthanized. Animals are weighed once a week.

Treatment Protocols

Diet

Animals are fed a custom diet prior to or after coronary ligation. The length of treatment will vary with the study. Doses are calculated based on the average consumption of feed per day. Rat weights are monitored during the study. Feed not consumed is weighed to estimate consumption rates.

Gavage

Animals are dosed orally by gavage. Length and frequency of treatment will vary with the study. A standard rat gavage tube (Popper & Sons Inc, NY) is attached to a 3-cc hypodermic syringe. The animal is held by the shoulder in a vertical position. The feeding tube is placed into the mouth then advanced until it reaches the stomach (the approximate insertion length of the tube is measured prior to the feeding). The content of the syringe is slowly delivered, and then the tube is withdrawn.

Drinking Water

Compound can also be dissolved in the drinking water. Water consumption is monitored. In the case of a bitter tasting compound, flavoring agents may be added to the water of both vehicle and treated groups. In the case of insoluble compounds, solubilizing agents may be used (i.e. 0.015% cremophor.0.015% alcohol).

Alzet Pumps

Alzet pumps can be implanted using aseptic techniques into the peritoneum or subcutaneously behind the shoulder blades. Pumps are implanted using Isoflurane anesthesia. Serial implantation can be used for extended studies.

Measurements

In Vivo

After 6–12 weeks the animals are anesthetized with Ketamine/Xylazine (95 mg/kg and 5 mg/kg), and a catheter is placed in the right carotid artery and advanced into the left ventricle for hemodynamic measurements. The catheter is attached to a pressure transducer calibrated against a mercury manometer immediately prior to use. Recordings are made by a DATAQ data analysis system. Pressure traces are recorded and analyzed for heart rate, left ventricular systolic and diastolic pressure, left ventricular developed pressure, and dP/dt max and min. An average of at least five peaks is used to determine values for left ventricular systolic and end diastolic pressure. Left ventricular developed pressure is determined by subtracting end diastolic pressure from left ventricular systolic pressure. Heart rate is determined from the frequency spectrum of a 5 second sample. After measurements are taken, 2 ml blood is removed and placed in serum and plasma tubes for possible analysis.

Ex Vivo

After removal, the heart is placed in cold saline to stop the beating, then trimmed and weighed. Heart weight is presented as total weight and as a percentage of total body weight. After removal of the heart, lungs and liver are weighed and dried overnight for determination of wet to dry ratios.

The heart is sliced and slice #3 is incubated in 1% triphenyltetrazolium chloride (TTC) in 0.9% saline for 20 minutes at 37° C. Tetrazolium reacts with NADH in the presence of dehydrogenase enzymes causing viable tissue to stain a deep red color that is easily distinguished from the infarcted pale-unstained necrotic tissue. The slice is placed apex side down in the lid of a small petri dish for the staining procedure. The bottom of the dish is placed over the slice to keep it flat. The slice is photographed. The areas of infarcted tissue, left and right ventricle are determined using a computerized image analysis system. Infarct size is expressed as a percentage of the total ventricle. Total areas of the left and right ventricle are measured. The remaining sections are divided into right and left ventricle and frozen for TBARS and glutathione assays.

Statistical Analysis

Group data is presented as means +/−SEM. Comparisons between treatment groups are made using ANOVA with $p<0.05$ considered significant. Post hoc comparisons use either Dunnett's test or Tukey's test. Survival curves are generated using Graph Pad Prism. For each X value (time) Prism shows the fraction still alive. It also shows standard error. Prism calculates survival fractions using the product limit or Kaplan-Meier method.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention.

What is claimed is:

1. A composition comprising an isolated compound of the formula:

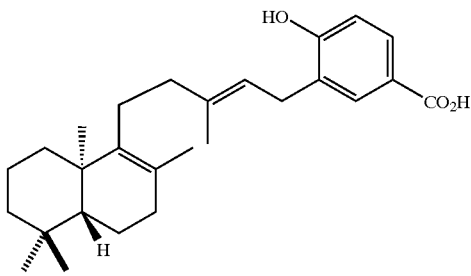

or an isomer, racemate or racemic mixture thereof, or a pharmaceutically acceptable salt thereof.

2. A composition comprising an isolated compound of the formula:

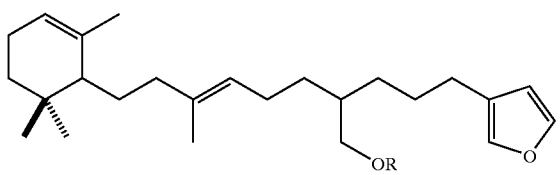

or an isomer, racemate or racemic mixture thereof, or a pharmaceutically acceptable salt thereof, wherein R =—SO$_3$Na or —SO$_3$H.

3. A composition comprising an isolated compound of the formula:

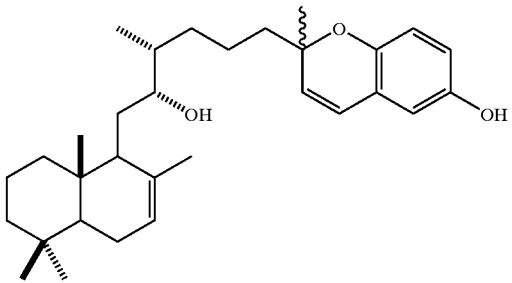

or an isomer, racemate or racemic mixture thereof, or a pharmaceutically acceptable salt thereof.

4. A pharmaceutical composition comprising a pharmaceutically acceptable carrier, and a compound having a formula of:

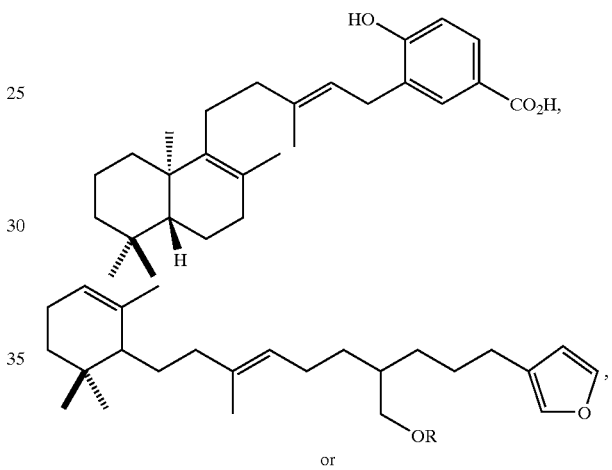

racemate or racemic mixture thereof, or a pharmaceutically acceptable salt thereof, wherein R=—SO$_3$Na or —SO$_3$H.

5. The pharmaceutical composition of claim 4, wherein said compound is present in an amount effective to treat a lipoxygenase-mediated condition.

6. The pharmaceutical composition of claim 5, wherein the lipoxygenase-mediated condition is an ischemia.

7. The pharmaceutical composition of claim 5, wherein said lipoxygenase mediated condition is a stroke.

8. The pharmaceutical composition of claim 5, wherein said lipoxygenase-mediated condition is an inflammatory condition.

9. A method for inhibiting a lipoxygenase, comprising contacting a cell with an effective amount of a compound having a formula of:

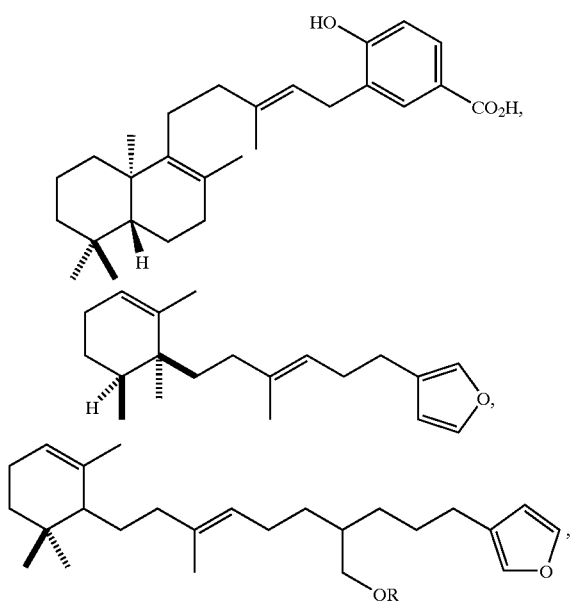
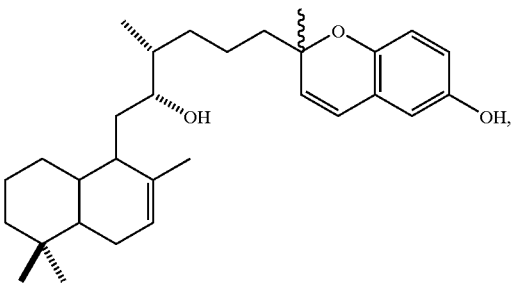
or an isomer, racemate or racemic mixture thereof, or a pharmaceutically acceptable salt thereof, wherein R=—SO₃Na or —SO₃H.
* * * * *

UNITED STATES PATENT AND TRADEMARK OFFICE
CERTIFICATE OF CORRECTION

PATENT NO. : 6,750,247 B2
DATED : June 15, 2004
INVENTOR(S) : Phillip Crews

It is certified that error appears in the above-identified patent and that said Letters Patent is hereby corrected as shown below:

Column 43,
Lines 37 and 54, the words, "A composition comprising an" should be replaced with the word -- An --.
Lines 52 and 65, the words "racemate or racemic mixture thereof" should be replaced with the words -- racemic or non-racemic mixtures of an isomer --.

Column 44,
Line 1, the words "A composition comprising an" should be replaced with the word -- An --.
Lines 16 and 53, the words "racemate or racemic mixture thereof" should be replaced with the words -- racemic or non-racemic mixtures of an isomer --.
Line 57, the words -- , wherein the condition is inflammation -- should be added after the word "condition" and before the ".".
Lines 58-59, the words "claim 5, wherein the" should be replaced with the words -- claim 4, wherein said compound is present in an amount effective to treat --.
Line 59, the words "condition is an" following the word "mediated" and before the word "ischemia" should be removed.
Lines 60-61, the words "claim 5, wherein said lipoxygenase mediated condition is a stroke" should be replaced with the words -- claim 4, wherein said compound is present in an amount effective to treat a lipoxygenase-mediated neurodegenerative disorder --.
Lines 62-64, the words "claim 5, wherein said lipoxygenase mediated condition is an inflammatory condition" should be replaced with the words -- claim 5, wherein the inflammation is an inflammation of asthma, psoriasis, inflammatory bowel disease, renal disease, rheumatoid arthritis, osteoarthritis, pre-menstrual syndrom, or aging --
Lines 65-66, the words "inhibiting a lipoxygenase, comprising contacting a cell with an" should be replaced with the words -- treating a subject suffering from lipoxygenase-mediated inflammation comprising administering to said subject a therapeutically --.

Column 46,
Line 18, the words "racemate or racemic mixture thereof" should be replaced with the words -- racemic or non-racemic mixtures of an isomer --.

UNITED STATES PATENT AND TRADEMARK OFFICE
CERTIFICATE OF CORRECTION

PATENT NO. : 6,750,247 B2
DATED : June 15, 2004
INVENTOR(S) : Phillip Crews

It is certified that error appears in the above-identified patent and that said Letters Patent is hereby corrected as shown below:

Column 46, claims 10 to 19 should be added:

-- 10. A method for treating a subject suffering from a lipoxygenase-mediated ischemia, comprising administering to said subject a therapeutically effective amount of a compound having a formula of:

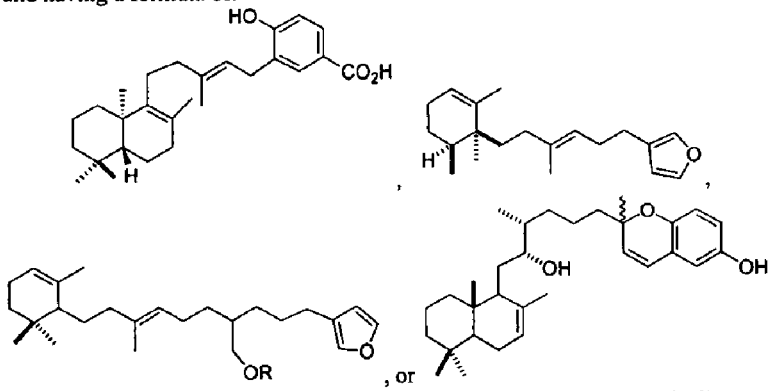

or an isomer, racemic or non-racemic mixtures of an isomer, or a pharmaceutically acceptable salt thereof, wherein R = -SO$_3$Na or -SO$_3$H.

11. The method of claim 9, wherein the lipoxygenase-mediated inflammation is inflammation of asthma, psoriasis, inflammatory bowel disease, renal disease, rheumatoid arthritis, osteoarthritis, pre-menstrual syndrome, or aging.

12. The method of claim 9, wherein said lipoxygenase-mediated inflammation is inflammation of atherosclerosis, diabetes, asthma, cardiopulmonary inflammatory disorders, heart failure, muscle fatigue, allograft tissue rejection, or organ transplant rejection.

13. The method of claim 10, wherein said lipoxygenase-mediated ischemia is cerebral ischemia, retinal ischemia, myocardial ischemia, ischemia of myocardial infarction, ischemia of congestive heart failure, or ischemia of post surgical cognitive dysfunction.

14. A method for treating a subject suffering from a lipoxygenase-mediated neurodegenerative disorder, comprising administering to said subject a therapeutically effective amount of a compound having a formula of:

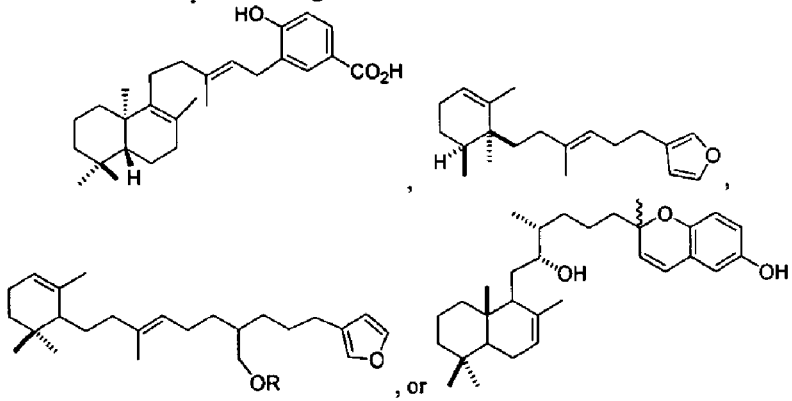

or an isomer, racemic or non-racemic mixtures of an isomer, or a pharmaceutically acceptable salt thereof, wherein R = -SO$_3$Na or -SO$_3$H.

UNITED STATES PATENT AND TRADEMARK OFFICE
CERTIFICATE OF CORRECTION

PATENT NO.    : 6,750,247 B2
DATED         : June 15, 2004
INVENTOR(S)   : Phillip Crews It is certified that error appears in the above-identified patent and that said Letters Patent is hereby corrected as shown below:

Column 44, (cond't),

15. The method of claim 14, wherein the lipoxygenase-mediated neurodegenerative disorder is Alzheimer's, dementia, Parkinson's disease, or a peripheral neuropathy.
    16. The method of claim 9, wherein the compound has the formula of:

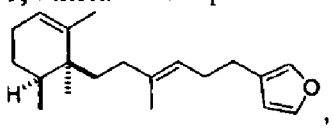

or an isomer, racemic or non-racemic mixtures of an isomer, or a pharmaceutically acceptable salt thereof, wherein R = -SO$_3$Na or -SO$_3$H.
    17. The method of claim 16, wherein the lipoxygenase-mediated inflammation is inflammation of asthma, psoriasis, inflammatory bowel disease, renal disease, rheumatoid arthritis, osteoarthritis, or pre-menstrual syndrome.
    18. The method of claim 16, wherein the lipoxygenase-mediated inflammation is inflammation of atherosclerosis, diabetes, asthma, cardiopulmonary inflammatory disorders, heart failure, muscle fatigue, allograft tissue rejection, or organ transplant rejection.
    19. The method of claim 16, wherein the lipoxygenas- mediated inflammation is inflammation of aging. --

Signed and Sealed this

Twenty-ninth Day of March, 2005

JON W. DUDAS
*Director of the United States Patent and Trademark Office*

UNITED STATES PATENT AND TRADEMARK OFFICE
CERTIFICATE OF CORRECTION

PATENT NO. : 6,750,247 B2  
APPLICATION NO. : 10/159772  
DATED : June 15, 2004  
INVENTOR(S) : Phillip Crews et al.

Page 1 of 1

It is certified that error appears in the above-identified patent and that said Letters Patent is hereby corrected as shown below:

<u>On the title page Item (73):</u>
The assignee "Galileo Laboratories, Inc., Santa Clara, CA (US)" should be replaced with -- The Regents of the University of California, Oakland, CA (US); Galileo Pharmaceuticals, Inc., Santa Clara, CA (US) --.

Signed and Sealed this

Twenty-sixth Day of August, 2008

JON W. DUDAS  
*Director of the United States Patent and Trademark Office*